United States Patent [19]

Ohba et al.

[11] Patent Number: 5,312,929

[45] Date of Patent: May 17, 1994

[54] 2-OXO-3-PYRROLINE DERIVATIVES, PROCESS FOR THEIR PRODUCTION AND HERBICIDAL COMPOSITION

[75] Inventors: Nobuyuki Ohba; Toshihiro Nagata; Akira Takeuchi; Shigehiko Tachikawa; Yasunori Ogawa, all of Shizuoka, Japan

[73] Assignees: Kumiai Chemical Industry Co., Ltd.; Ihara Chemical Industry Co., Ltd., both of Tokyo, Japan

[21] Appl. No.: 995,828

[22] Filed: Dec. 23, 1992

[30] Foreign Application Priority Data

Feb. 17, 1992 [JP] Japan ................................. 4-061483
Feb. 17, 1992 [JP] Japan ................................. 4-061484

[51] Int. Cl.$^5$ .................... C07D 207/27; A01N 43/36
[52] U.S. Cl. ................................. 548/551; 504/283; 548/547; 548/550
[58] Field of Search ................. 548/543, 550, 551; 504/283

[56] References Cited

U.S. PATENT DOCUMENTS 3,272,842  9/1966  Easton et al. .

FOREIGN PATENT DOCUMENTS 857684  2/1978  Belgium .
0372586  6/1990  European Pat. Off. .

*Primary Examiner*—David B. Springer
*Attorney, Agent, or Firm*—Oblon, Spivak, McClelland, Maier & Neustadt

[57] ABSTRACT

A herbicidal 2-oxo-3-pyrroline derivative having the formula:

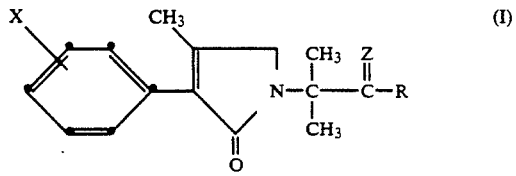

wherein X is a hydrogen atom or a halogen atom, Z is an oxygen atom or a group of the formula $=N-OR^1$ (wherein $R^1$ is a hydrogen atom, an alkyl group, a benzyl group or a phenyl group which is substituted by halogen atoms); and R is a hydrogen atom, an alkyl group, a benzyl group, a chloro-substituted benzyl group, a benzylidene methyl group, a group of the formula

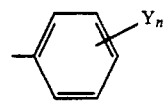

wherein Y is a hydrogen atom, a halogen atom, an alkyl group, a haloalkyl group or an alkoxy group, and n is an integer of from 1 to 3, or a group of the formula $ER^2$ wherein E is an oxygen atom, a sulfur atom or a group of the formula $>N-R^3$, wherein $R^3$ is a hydrogen atom, an alkyl group or an alkenyl group, and $R^2$ is a hydrogen atom, an alkyl group, a cycloalkyl group, an alkenyl group, an alkynyl group, a benzyl group, a phenylsulfonyl group or a group of the formula

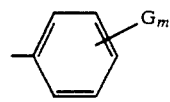

wherein G is defined in the specification and m is an integer of 1-5.

7 Claims, No Drawings

2-OXO-3-PYRROLINE DERIVATIVES, PROCESS FOR THEIR PRODUCTION AND HERBICIDAL COMPOSITION

The present invention relates to 2-oxo-3-pyrroline derivatives and a herbicidal composition containing one or more of them as an active ingredient.

Heretofore, 2-oxo-3-pyrroline derivatives have been known to have herbicidal activities. For example, U.S. Pat. No. 3,272,842 discloses that compounds having the following formula:

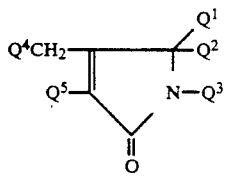

wherein each of $Q^1$ and $Q^2$ is a lower alkyl group or a phenyl group which may be substituted, $Q^3$ is a hydrogen atom, a lower alkyl group, a cycloalkyl group, an alkoxyalkyl group or a tetrahydrofurfuryl group, $Q^4$ is a hydrogen atom, a lower alkyl group, a phenyl group or a naphthyl group, and $Q^5$ is a phenyl group which may be substituted, a phenoxy group, a phenylthio group, a naphthyl group, a naphthyloxy group, a naphthylthio group or a thienyl group, are effective as selective herbicides for soil treatment and foliage treatment.

Further, Belgian Patent 857,684 discloses that compounds having the following formula:

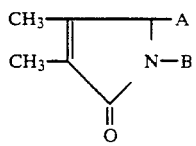

wherein A is a hydroxyl group, a halogen atom or an acyloxy group, and B is an aryl group, an aralkyl group or a hetero ring, are effective as selective herbicides.

Furthermore, Japanese Unexamined Patent Publication No. 204855/1991 (U.S. Pat. No. 5,006,157) discloses that compounds having the following formula:

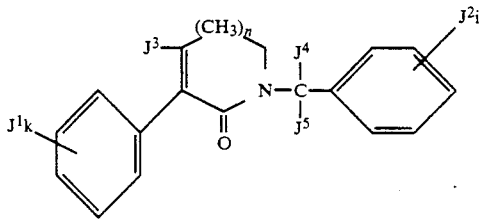

wherein $J^1$ is a hydrogen atom, a halogen atom, an alkyl group, a haloalkyl group, an alkoxy group, a haloalkoxy group, an alkylthio group or a nitro group, $J^2$ is a hydrogen atom, a halogen atom, an alkyl group, a cycloalkyl group, an alkenyl group, an alkynyl group, a haloalkyl group, a phenyl group, an alkoxy group, a cycloalkoxy group, an alkenyloxy group, an alkynyloxy group, a benzyloxy group, a phenoxy group, a haloalkoxy group, an alkoxyalkoxy group, a cyanoalkoxy group, an alkylthio group, an alkenylthio group, an alkynylthio group, a benzylthio group, a phenylthio group, a group of the formula $—W—CH(E^1)COOE^2$ (wherein W is an oxygen atom or a sulfur atom, $E^1$ is a hydrogen atom or an alkyl group, and $E^2$ is an alkyl group), a group of the formula $—N(E^3)E^4$ (wherein each of $E^3$ and $E^4$ is a hydrogen atom or an alkyl group), an alkylsulfonyl group, a group of the formula $—SO_2N(E^5)E^6$ (wherein each of $E^5$ and $E^6$ is a hydrogen atom or an alkyl group), an alkylcarbonyl group, a nitro group, a cyano group or a hydroxyl group, $J^3$ is a hydrogen atom or an alkyl group, each of $J^4$ and $J^5$ which may be the same or different, is an alkyl group, m is 0 or 1, i is an integer of from 1 to 5, k is an integer of from 1 to 2, or $J^4$ and $J^5$ may form a ring together with the adjacent carbon atom, are effective as herbicides.

In recent years, it is strongly desired to develop a herbicide having selective herbicidal activities to kill weeds only without presenting phytotoxicity against crop plants. Further, in order to avoid the herbicide to remain excessively in the environment, it is desired to develop a herbicide which shows excellent herbicidal effects at a low dose.

The above-mentioned compounds known as conventional herbicides do not necessarily fully satisfy such requirements.

In order to solve the above-mentioned problems, the present inventors have synthesized many 2-oxo 3-pyrroline derivatives and have studied their usefulness. As a result, it has been found that the compound of the present invention having an isobutyric acid derivative at the 1-position of the 2-oxo-3-pyrroine ring has excellent herbicidal activities and selectivity suitable for the above object. The present invention has been accomplished on the basis of this discovery.

The present invention provides a 2-oxo-3-pyrroline derivative having the formula:

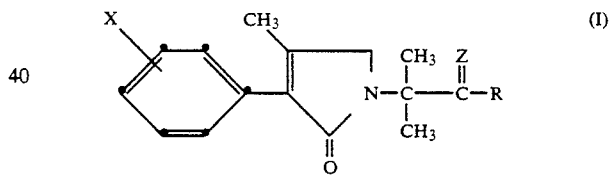

wherein X is a hydrogen atom or a halogen atom, Z is an oxygen atom or a group of the formula $=N—OR^1$ (wherein $R^1$ is a hydrogen atom, an alkyl group, a benzyl group or a phenyl group which is substituted by halogen atoms); and R is a hydrogen atom, an alkyl group, a benzyl group, a chloro-substituted benzyl group, a benzylidene methyl group, a group of the formula

(wherein Y is a hydrogen atom, a halogen atom, an alkyl group, a haloalkyl group or an alkoxy group, and n is an integer of from 1 to 3) or a group of the formula $ER^2$ {wherein E is an oxygen atom, a sulfur atom or a group of the formula $>N—R^3$ (wherein $R^3$ is a hydrogen atom, an alkyl group or an alkenyl group), and $R^2$ is a hydrogen atom, an alkyl group, a cycloalkyl group, an alkenyl group, an alkynyl group, a benzyl group, a phenylsulfonyl group or a group of the formula

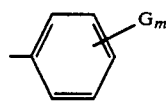

(wherein G is a hydrogen atom, a halogen atom, an alkyl group, a haloalkyl group, an alkoxy group, a haloalkoxy group, a methylenedioxy group, an alkylthio group, an alkylsulfonyl group, a phenoxy group, an alkoxycarbonyl group, an acyl group, a nitro group, a hydroxyl group, a cyano group or a dimethylamino group, and m is an integer of from 1 to 5}.

The compound of the present invention can be produced by the following processes. However, the method for its production is not limited to such specific processes.

PROCESS 1

Reaction Scheme 1

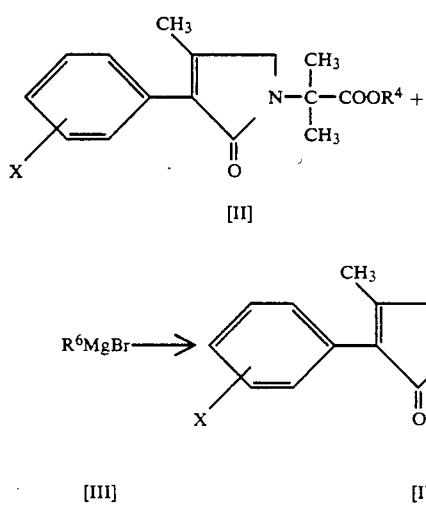

In the above formulas, X is as defined above, $R^4$ is an alkyl group, and $R^5$ is an alkyl group, an alkenyl group, an alkynyl group, a benzyl group which may be substituted or a phenyl group which may be substituted.

The compound of the present invention represented by the formula (IV) can be produced by reacting a compound of the formula (II) with an organic magnesium compound of the formula (III).

Here, an ether such as tetrahydrofuran or ethyl ether can be used as the solvent. The above reaction is preferably conducted under a nitrogen stream within a temperature range of from 0° C. to the boiling point of the solvent for from 1 to 24 hours. The desired compound can be obtained from the reaction solution by a conventional method and can be purified by recrystallization or by column chromatography, as the case requires.

PROCESS 2

Reaction Scheme 2

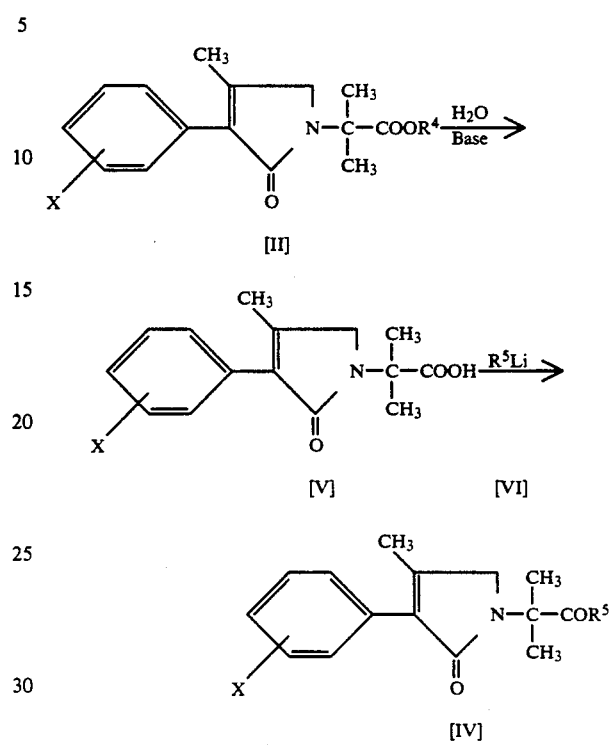

In the above formulas, X, $R^4$ and $R^5$ are as defined above.

The compound of the present invention represented by the formula (IV), can be produced by reacting a lithium compound (VI) to a 2-(4-methyl-2-oxo-3-phenyl-3-pyrrolin-1-yl) isobutyric acid (V) obtained by alkali hydrolysis of an isobutyrate of the formula (II).

The hydrolysis of the compound of the formula (II) is conducted by using an aqueous solution of sodium hydroxide or potassium hydroxide as the base. As the solvent, water or a water-soluble solvent not susceptible to hydrolysis, such as dioxane, methanol or ethanol, may be used. The reaction is conducted at a temperature within a range of from room temperature to the boiling point of the solvent and will be completed in from 0.5 to 10 hours. The desired compound can be obtained from the reaction solution by a conventional method. Further, it may be purified by recrystallization or by column chromatography, as the case requires.

For the reaction of the compound (V) with the lithium compound (VI), an ether such as tetrahydrofuran or ethyl ether may be used as the solvent. The reaction can be conducted at a temperature within a range of $-10°$ C. to the boiling point of the solvent for from 1 to 24 hours. The reaction is preferably conducted under a nitrogen atmosphere. The desired compound can be obtained from the reaction solution by a conventional method. Further, it may be purified by recrystallization or by column chromatography, as the case requires.

PROCESS 3

Reaction Scheme 3

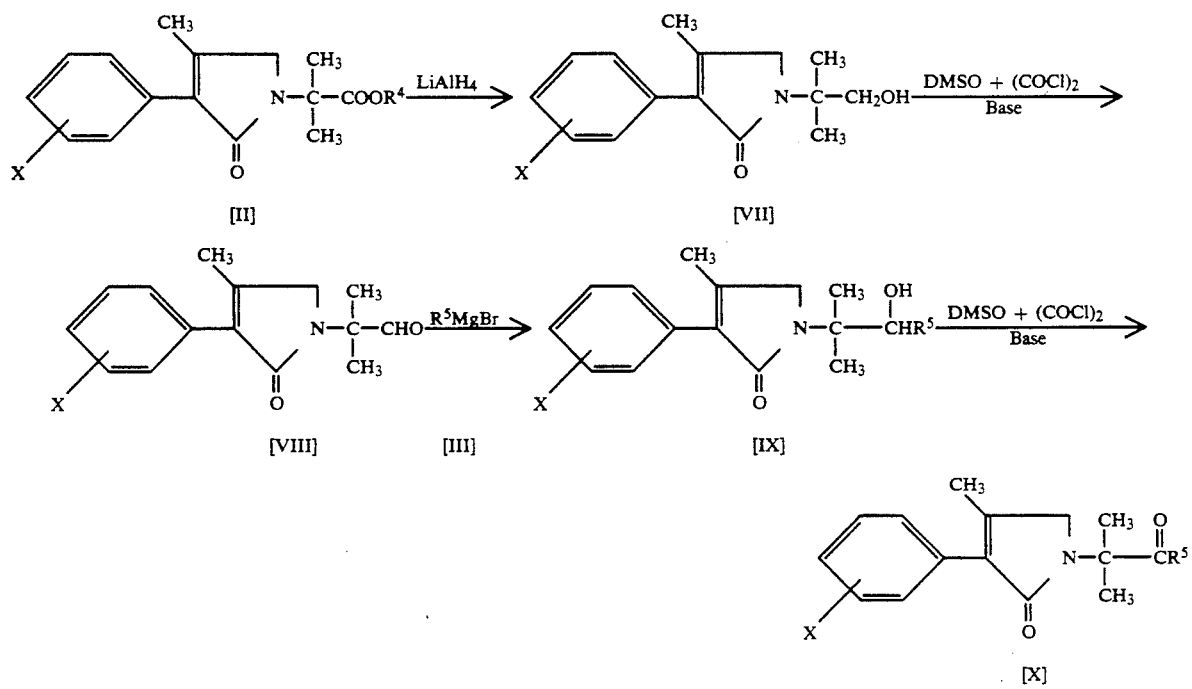

In the above formulas, X, $R^4$ and $R^5$ are as defined above.

Firstly, the compound of the formula (II) is reduced with lithium aluminum hydride to obtain a compound of the formula (VII).

Here, an ether such as diethyl ether, tetrahydrofuran or dioxane may be used as the solvent. The reaction can be conducted at a temperature within a range of from −70° C. to room temperature and will be completed in from 0.5 to 10 hours. The desired compound can be obtained from the reaction solution by a conventional method. Further, it may be purified by recrystallization or by column chromatography, as the case requires.

Then, the compound (VII) obtained by the above reaction, is oxidized with dimethyl sulfoxide and oxalyl dichloride to obtain a compound of the formula (VIII). This reaction is conducted in the presence of a base. As the base, an organic amine such as triethylamine or 1,8-diazabicyclo[5.4.0]undec-7-ene (DBU), or an inorganic base such as sodium hydroxide, potassium hydroxide, sodium hydrogen carbonate or potassium carbonate may be used. As the solvent, a halogenated hydrocarbon such as chloroform or dichloromethane may be used. The reaction can be conducted within a temperature range of from −70° C. to room temperature for from 0.5 to 10 hours. The desired compound can be obtained from the reaction solution by a conventional method. Further, it may be purified by recrystallization or by column chromatography, as the case requires.

Further, a magnesium compound of the formula (III) is reacted to the compound (VIII) obtained by the above reaction, to obtain a compound of the formula (IX).

As the solvent, an ether such as tetrahydrofuran or ethyl ether, may be used. The reaction is conducted at a temperature within a range of from 0° C. to the boiling point of the solvent for from 0.5 to 10 hours. The desired compound can be obtained from the reaction solution by a conventional method. Further, it may be purified by recrystallization or by column chromatography, as the case requires.

Further, the compound (IX) obtained by the above reaction is oxidized again with dimethyl sulfoxide and oxalyl dichloride to obtain a compound of the present invention represented by the formula (X).

For this reaction, a base is required, and an organic amine such as triethylamine or DBU, or an inorganic base such as sodium hydroxide or potassium hydroxide, may be used as such a base. As the solvent, a halogenated hydrocarbon such as chloroform or dichloromethane can be used. The reaction is conducted within a temperature range of from −70° C. to room temperature for from 0.5 to 10 hours. The desired compound can be obtained from the reaction solution by a conventional method. Further, it can be purified by recrystallization or by column chromatography, as the case requires.

PROCESS 4

Reaction Scheme 4

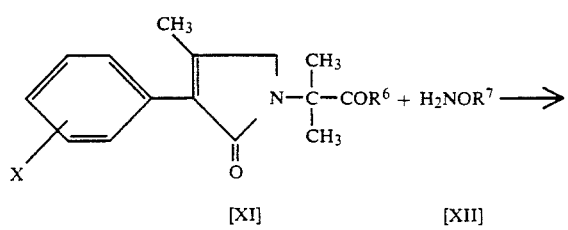

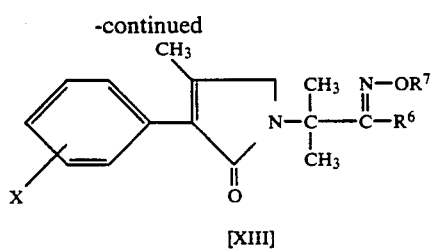

[XIII]

In the above formulas, X is as defined above, $R^6$ is an alkyl group or a phenyl group which may be substituted, and $R^7$ is a hydrogen atom, an alkyl group, a phenyl group which may be substituted or a benzyl group.

The compound of the present invention represented by the formula (XIII) can be produced by reacting a ketone derivative of the formula (XI) with the compound (XII). When a hydrochloride of compound (XII) is employed, a base may be used.

As the base, an organic amine such as triethylamine or DBU, an inorganic base such as sodium hydroxide, potassium hydroxide or potassium carbonate, or sodium acetate, may be employed. As the solvent, an alcohol such as methanol or ethanol, an ether such as ethyl ether, tetrahydrofuran or dioxane, a halogenated hydrocarbon such as dichloromethane or chloroform, an aprotic polar solvent such as N,N-dimethylformamide (DMF), N,N-dimethylacetamide (DMAc) or dimethyl sulfoxide, or water, may be used. The reaction is conducted within a temperature range of from 0° C. to the boiling point of the solvent for from 1 to 24 hours. The desired compound can be obtained from the reaction solution by a conventional method. Further, it may be purified by recrystallization or by column chromatography, as the case requires.

PROCESS 5

Reaction Scheme 5

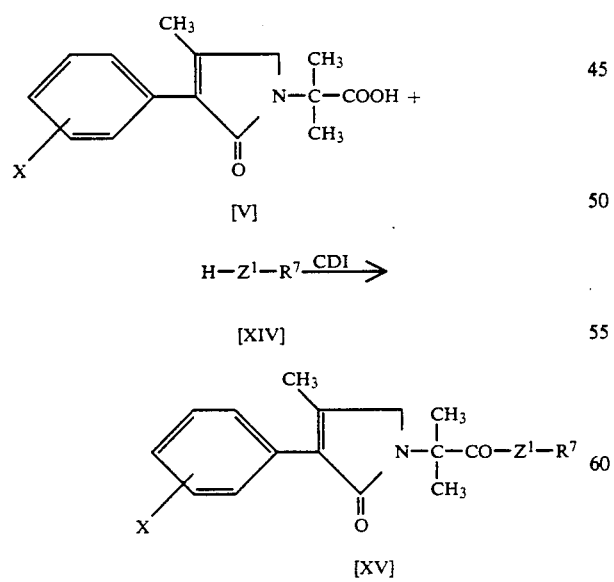

[XV]

In the above formulas, $Z^1$ is an oxygen atom, a sulfur atom or a group of the formula —N($R^2$)—, $R^7$ is an alkyl group, an alkenyl group, a benzyl group, a phenyl group which may be substituted or a phenyl sulfonyl group, and X and $R^2$ are as defined above.

The compound of the present invention represented by the formula (XV) can be produced by reacting carbonyl diimidazole (CDI) to a compound of the formula (V), followed by a reaction with a compound of the formula (XIV) or its salt in the presence or absence of a base.

Here, as the solvent, a halogenated hydrocarbon such as dichloromethane, chloroform or carbon tetrachloride, an ether such as diethyl ether, tetrahydrofuran or dioxane, a hydrocarbon such as n-hexane, benzene or toluene, an aliphatic ketone such as acetone or methyl ethyl ketone, or an aprotic polar solvent such as acetonitrile, DMF or DMAc, may be used. This reaction is conducted within a temperature range of from room temperature to the boiling point of the solvent and will be completed in from 0.5 to 24 hours. The desired compound can be obtained from the reaction solution by a conventional method. Further, it can be purified by recrystallization or by column chromatography, as the case requires.

Here, as the base, an organic amine such as trimethylamine, triethylamine, DBU, pyridine, picoline or quinoline, an alkali metal such as sodium or potassium, a metal hydride such as sodium hydride or potassium hydride, a metal alcoholate such as sodium methylate, sodium ethylate or potassium t-butylate, or an inorganic base such as sodium hydroxide, potassium hydroxide, sodium carbonate or potassium carbonate, may be used. Further, as the solvent, an ether such as diethyl ether, tetrahydrofuran or dioxane, a hydrocarbon such as n-hexane, benzene or toluene, an alcohol such as methanol or ethanol, or an aprotic polar solvent such as acetonitrile, DMF or DMAc, may be employed. The reaction can be conducted at a temperature within a range of from 0° C. to the boiling point of the solvent.

PROCESS 6

Reaction Scheme 6

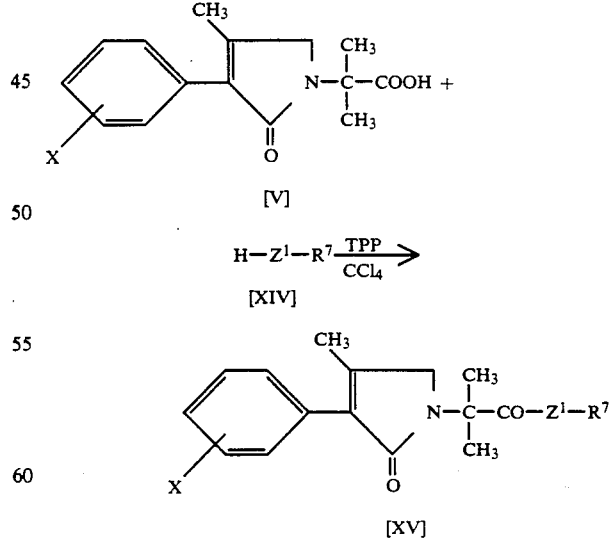

[XV]

In the above formulas, X, $Z^1$ and $R^7$ are as defined above.

The compound of the present invention represented by the formula (XV) can be produced by reacting triphenyl phosphine (TPP) and carbon tetrachloride to a compound of the formula (V), followed by a reaction with a compound of the formula (XIV) or its salt. No base is required for the reaction, but to neutralize hydrogen chloride formed, a base may be used in an amount of from 0.1 to 1 time the amount of the starting material (V). When $Z^1$ is $-N(R_2)-$, the material of the formula (XIV) may be used in excess.

Here, as the base, an organic amine such as triethylamine, DBU, pyridine, picoline or quinoline, may be used. As the solvent, a halogenated hydrocarbon such as dichloromethane, chloroform or carbon tetrachloride, an ether such as diethyl ether, tetrahydrofuran or dioxane, a hydrocarbon such as n-hexane, benzene or toluene, or an aprotic polar solvent such as acetonitrile, DMF or DMAc, may be used. The reaction is conducted within a temperature range of from an ice-cooled temperature to the boiling point of the solvent, and it will be completed in from 0.5 to 10 hours. The desired product can be obtained by filtering off insoluble materials in the reaction solution, followed by concentration and purification by recrystallization or by column chromatography.

PROCESS 7 compound of the formula (XVI) with a compound of the formula (XVII) in the presence of a base.

Here, as the base, a metal hydride such as sodium hydride or potassium hydride, a metal alcoholate such as sodium methylate or sodium ethylate, an organic amine such as triethylamine, DBU, pyridine, picoline or quinoline, or an inorganic base such as sodium hydroxide, potassium hydroxide, sodium carbonate or potassium carbonate, may be employed. As the solvent, a halogenated hydrocarbon such as dichloromethane, chloroform or carbon tetrachloride, an ether such as diethyl ether, tetrahydrofuran or dioxane, a hydrocarbon such as n-hexane, benzene or toluene, an aliphatic ketone such as acetone or methyl ethyl ketone, an alcohol such as methanol or ethanol, or an aprotic polar solvent such as acetonitrile, DMF or DMAc, may be used. This reaction is conducted within a temperature range of from 0° C. to the boiling point of the solvent, and will be completed in from 1 to 10 hours. The desired compound can be obtained from the reaction solution by a conventional method. Further, it may be purified by crystallization or by column chromatography, as the case requires.

PROCESS 8

Reaction Scheme 7

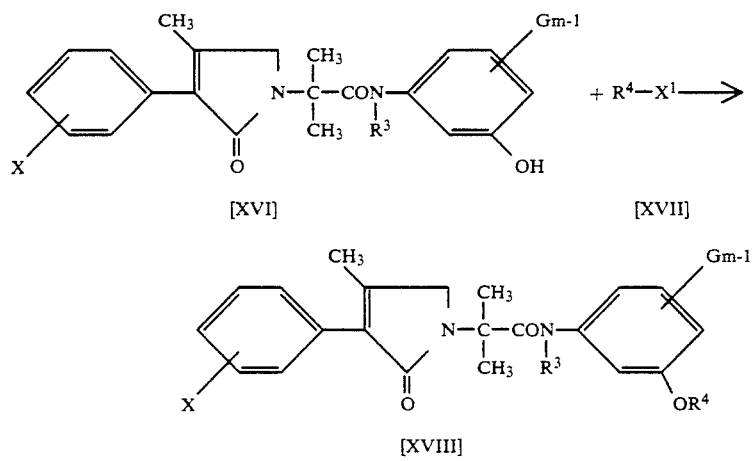

In the above formulas, $X^1$ is a halogen atom, and $R^3$,

Reaction Scheme 8

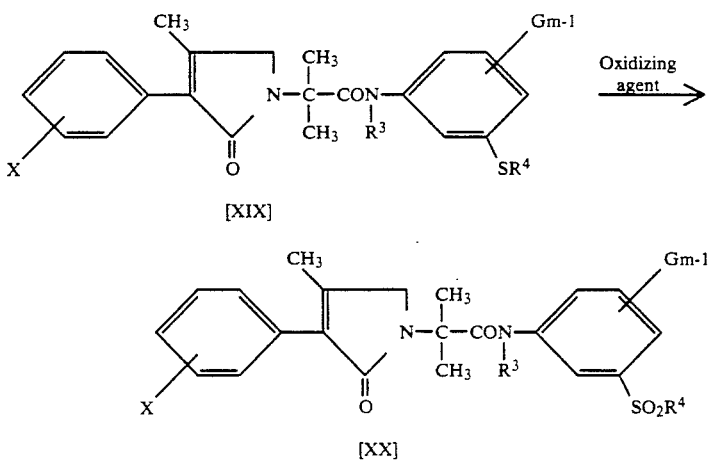

$R^4$, X, G and m are as defined above.

The compound of the present invention represented by the formula (XVIII) can be produced by reacting a In the above formulas, $R^3$, $R^4$, X, G and m are as defined above.

The compound of the present invention represented by the formula (XX) can be produced by oxidizing a compound of the formula (XIX) with a suitable oxidizing agent.

Here, as the oxidizing agent, aqueous hydrogen peroxide, a perbenzoate or OXONE (trademark) may, for example, be used. As the solvent, a halogenated hydrocarbon such as dichloromethane, chloroform or carbon tetrachloride, a hydrocarbon such as n-hexane, benzene or toluene, an aliphatic ketone such as acetone or methyl ethyl ketone, an alcohol such as methanol or ethanol, or an aprotic polar solvent such as acetonitrile, DMF, DMAc, or water, may be used. This reaction is conducted within a temperature range of from 0° C. to the boiling point of the solvent and will be completed in from 1 to 10 hours. The desired compound can be obtained from the reaction solution by a conventional method. Further, it may be purified by recrystallization or by column chromatography, as the case requires.

PROCESS 9

Reaction Scheme 9

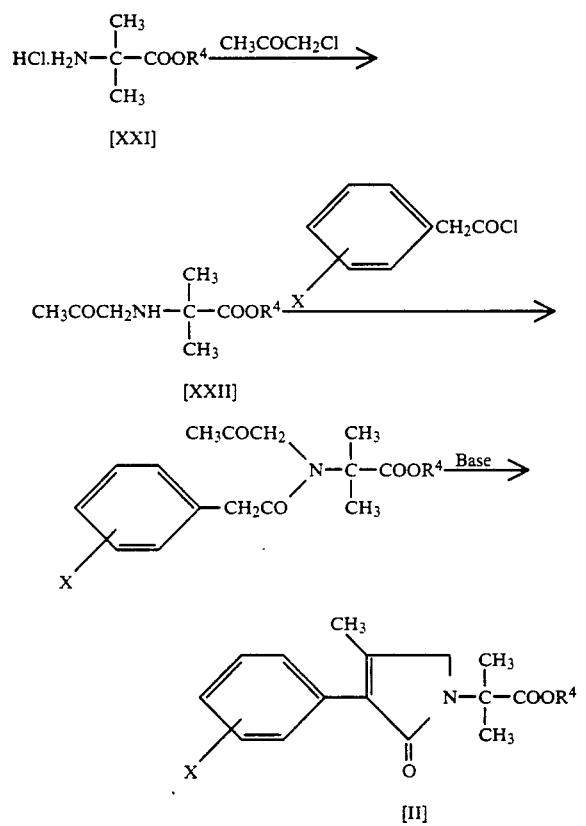

In the above formulas, $R^4$ is an alkyl group, and X is as defined above.

Firstly, a 2-aminoisobutylate hydrochloride of the formula (XXI) and monochloroacetone are reacted to produce a compound of the formula (XXII).

As the base, an organic amine such as triethylamine, DBU, pyridine, picoline or quinoline, or an inorganic base such as sodium hydroxide, potassium hydroxide, sodium carbonate or potassium carbonate, may be used. As the solvent, a halogenate hydrocarbon such as dichloromethane, chloroform or carbon tetrachloride, an ether such as diethyl ether, tetrahydrofuran or dioxane, a hydrocarbon such as n-hexane, benzene or toluene, an aliphatic ketone such as acetone or methyl ethyl ketone, or an aprotic polar solvent such as acetonitrile, DMF or DMAc, may be used. The above reaction is conducted within a temperature range of from room temperature to the boiling point of the solvent under nitrogen stream, and will be completed in from 1 to 24 hours. The desired compound of the formula (XXII) can be obtained from the reaction solution by a conventional method.

Then, the compound of the formula (XXII) thus obtained, is reacted with a phenylacetyl chloride which may be substituted, to obtain a compound of the formula (XXIII).

As the base, an organic amine such as triethylamine, DBU, pyridine, picoline or quinoline, or an inorganic base such as sodium hydroxide, potassium hydroxide, sodium carbonate or potassium carbonate, can be used. As the solvent, a halogenated hydrocarbon such as dichloromethane, chloroform or carbon tetrachloride, an ether such as diethyl ether, tetrahydrofuran or dioxane, a hydrocarbon such as n-hexane, benzene or toluene, an aliphatic ketone such as acetone or methyl ethyl ketone, or an aprotic polar solvent such as acetonitrile, DMF or DMAc, may be used. The above reaction is conducted within a temperature range of from an ice-cooled temperature to 60° C. and will be completed in from 1 to 24 hours. The desired compound can be obtained from the reaction solution by a conventional method.

Then, the compound of the formula (XXIII) thus obtained, is subjected to inner molecular condensation in the presence of a base to obtain the compound of the present invention represented by the formula (II).

As the base, a metal alcoholate such as sodium methylate or sodium ethylate, or an organic amine such as triethylamine, DBU, pyridine, picoline or quinoline may also be used. As the solvent, a halogenated hydrocarbon such as dichloromethane, chloroform or carbon tetrachloride, an ether such as diethyl ether, tetrahydrofuran or dioxane, a hydrocarbon such as n-hexane, benzene or toluene, an alcohol such as methanol or ethanol, or an aprotic polar solvent such as acetonitrile, DMF or DMAc, may be used. The above reaction is conducted within a temperature range of from an ice-cooled temperature to the boiling point of the solvent and will be completed in from 0.5 to 10 hours. The desired compound can be obtained from the reaction solution by a conventional method. Further, it may be purified by recrystallization or by column chromatography, as the case requires.

Further, there is a method wherein an alkyl halide or the like is reacted to an isobutyric acid derivative for esterification.

The compounds of the formulas (VII), (VIII) and (IX) which are intermediates in Process 3, are novel compounds.

Typical examples of such intermediates of the formulas (VII) to (IX) are given in the following Table 1, and the methods for their preparation are shown in Reference Examples 3 and 4.

Then, typical examples of the compound of the present invention represented by the formula (I) will be given in Tables 2A, 2B, 3, 4A, 4B, 5A, 5B, 5C and 5D. Compound numbers in the Tables will be referred in the subsequent description.

TABLE 1

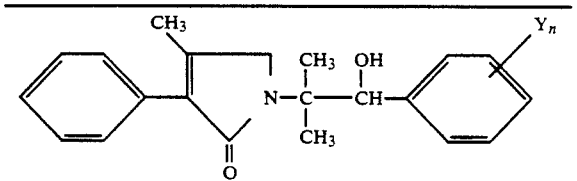

| Intermediate No. | $Y_n$ | Melting point (°C.) or Refractive index ($n_D^{20}$) |
|---|---|---|
| 1 | H | 48~49 |
| 2 | 3-CH$_3$ | 105~107 |
| 3 | 4-CH$_3$ | |
| 4 | 2-OCH$_3$ | 156~158 |
| 5 | 4-OCH$_3$ | 123~125 |
| 6 | 4-F | 151~153 |
| 7 | 2-Cl | |
| 8 | 3-OCH$_3$ | |
| 9 | 3-F | 135~136 |
| 10 | 2-CH$_3$ | 97~98 |
| 11 | 3,5-Cl$_2$ | 171~173 |

TABLE 2A

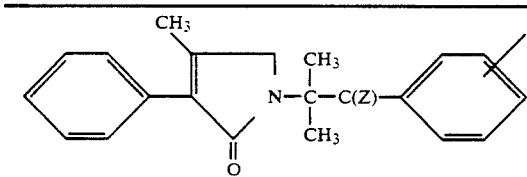

| Compound No. | Z | $Y_n$ | Melting point (°C.) or Refractive index ($n_D^{20}$) |
|---|---|---|---|
| 1 | O | H | 145~146 |
| 2 | O | 2-F | |
| 3 | O | 2-Cl | 97~100 |
| 4 | O | 2-CH$_3$ | 163~165 |
| 5 | O | 2-OCH$_3$ | 1.5740 |

TABLE 2A-continued

| Compound No. | Z | $Y_n$ | Melting point (°C.) or Refractive index ($n_D^{20}$) |
|---|---|---|---|
| 6 | O | 3-F | 156~159 |
| 7 | O | 3-Cl | 134~138 |
| 8 | =N—OH | 3-Cl | |
| 9 | =N—OCH$_3$ | 3-Cl | |
| 10 | O | 3-CH$_3$ | 129~132 |
| 11 | O | 3-C$_2$H$_5$ | |
| 12 | O | 3-CF$_3$ | |
| 13 | =N—OCH$_3$ | 3-CF$_3$ | |
| 14 | O | 3-OCH$_3$ | 160~163 |
| 15 | O | 3-OC$_2$H$_3$ | |
| 16 | O | 4-F | 140~144 |
| 17 | O | 4-Cl | 152~153 |
| 18 | O | 4-CH$_3$ | 157~161 |

TABLE 2B

| Compound No. | Z | $Y_n$ | Melting point (°C.) or Refractive index ($n_D^{20}$) |
|---|---|---|---|
| 19 | O | 4-OCH$_3$ | 136~139 |
| 20 | O | 2,5-Cl$_2$ | |
| 21 | =N—OCH$_3$ | 2,5-Cl$_2$ | |
| 22 | O | 3,4-Cl$_2$ | 156~159 |
| 23 | O | 3,5-F$_2$ | 161~163 |
| 24 | O | 3,5-Cl$_2$ | 157~160 |
| 25 | =N—OH | 3,5-Cl$_2$ | 266~228 |
| 26 | =N—OCH$_3$ | 3,5-Cl$_2$ | |
| 27 | =N—OC$_2$H$_5$ | 3,5-Cl$_2$ | |
| 28 | O | 3,5-(OCH$_3$)$_2$ | |
| 29 | O | 3,4,5-Cl$_3$ | |
| 30 | O | 3,5-Cl$_2$; 4-OCH$_3$ | |

TABLE 3

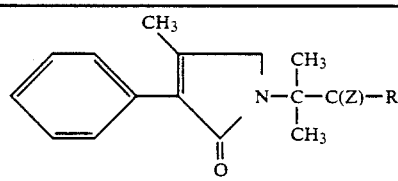

| Compound No. | R | Z | Melting point (°C.) or Refractive index ($n_D^{20}$) |
|---|---|---|---|
| 31 | H | =N—OH | |
| 32 | H | =N—O—(2,4-Cl$_2$-C$_6$H$_3$) | 129~132 |
| 33 | CH$_3$ | O | 160~163 |
| 34 | CH$_3$ | =N—OH | 206~208 |
| 35 | CH$_3$ | =N—OCH$_3$ | 111~113 |
| 36 | CH$_3$ | =N—OCH$_2$—C$_6$H$_5$ | 119~122 |

TABLE 3-continued

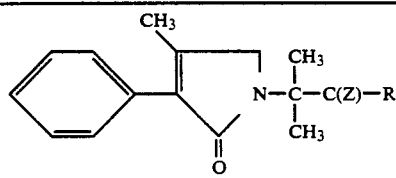

| Compound No. | R | Z | Melting point (°C.) or Refractive index ($n_D^{20}$) |
|---|---|---|---|
| 37 | i-$C_3H_7$ | O | 154~157 |
| 38 | n-$C_4H_9$ | O | 87~89 |
| 39 | n-$C_4H_9$ | =N—OH | 135~137 |
| 40 | n-$C_4H_9$ | =N—$OCH_3$ | 115~117 |
| 41 | t-$C_4H_9$ | O | 144~146 |
| 42 | Ph—$CH_2$ | O | 125~129 |
| 43 | (2-Cl)Ph—$CH_2$ | O | 105~109 |
| 44 | Ph—CH=CH (trans) | O | 162~166 |

TABLE 4A

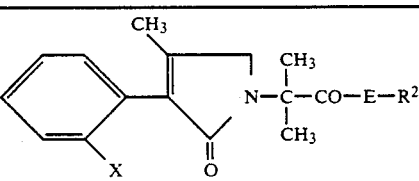

| Compound No. | X | E | $R^2$ | Melting point (°C.) or Refractive index ($n_D^{20}$) |
|---|---|---|---|---|
| 45 | H | O | H | 213~216 |
| 46 | H | O | $CH_3$ | 134~138 |
| 47 | H | O | $C_2H_5$ | 64~66 |
| 48 | H | O | n-$C_3H_7$ | 50~52 |
| 49 | H | O | i-$C_3H_7$ | 97~101 |
| 50 | H | O | n-$C_4H_9$ | 1.5338 |
| 51 | H | O | i-$C_4H_9$ | |
| 52 | H | O | t-$C_4H_9$ | |
| 53 | H | O | n-$C_6H_{13}$ | |
| 54 | H | O | $CH_2$=$CHCH_2$ | 65~67 |
| 55 | H | O | CH≡$CCH_2$ | 109~111 |
| 56 | H | O | Ph—$CH_2$ | 112~115 |
| 57 | H | O | Ph | 126~130 |
| 58 | H | S | $CH_3$ | 109~111 |
| 59 | H | S | $C_2H_5$ | 85~86 |

TABLE 4A-continued

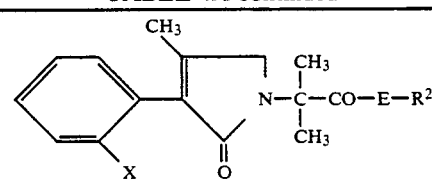

| Compound No. | X | E | $R^2$ | Melting point (°C.) or Refractive index ($n_D^{20}$) |
|---|---|---|---|---|
| 60 | H | S | n-$C_3H_7$ | |
| 61 | H | S | i-$C_3H_7$ | |
| 62 | H | S | n-$C_4H_9$ | |
| 63 | H | S | i-$C_4H_9$ | |

TABLE 4B

| Compound No. | X | E | $R^2$ | Melting point (°C.) or Refractive index ($n_D^{20}$) |
|---|---|---|---|---|
| 64 | H | S | t-$C_4H_9$ | |
| 65 | H | S | n-$C_6H_{13}$ | |
| 66 | H | S | $CH_2$=$CHCH_2$ | |
| 67 | H | S | CH≡$CCH_2$ | |
| 68 | H | S | Ph—$CH_2$ | 99-101 |

TABLE 4B-continued

| Compound No. | X | E | R² | Melting point (°C.) or Refractive index ($n_D^{20}$) |
|---|---|---|---|---|
| 69 | H | S | phenyl | 175–177 |
| 70 | H | NH | n-C₄H₉ | |
| 71 | H | NH | i-C₄H₉ | |
| 72 | H | NH | t-C₄H₉ | 137–140 |
| 73 | H | NH | c-C₆H₁₁ | |
| 74 | H | NH | phenyl-CH₂ | 159–162 |
| 75 | H | NH | phenyl-SO₂ | 168–171 |
| 76 | H | NCH₃ | CH₃ | 159–164 |
| 77 | H | NCH₃ | C₂H₅ | |
| 78 | H | NCH₃ | n-C₄H₉ | |
| 79 | H | NCH₃ | i-C₄H₉ | |
| 80 | H | NCH₃ | phenyl | 104–106 |
| 81 | H | NCH₃ | phenyl-CH₂ | |
| 82 | H | NC₂H₅ | C₂H₅ | |
| 83 | H | NC₃H₇-n | n-C₃H₇ | |
| 84 | H | NCH₂CH=CH₂ | CH₂=CHCH₂ | 112–115 |

TABLE 5A

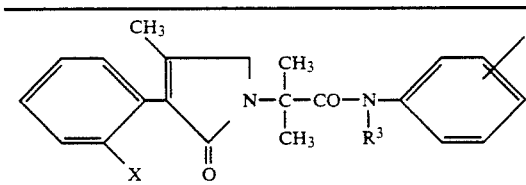

| Compound No. | X | G_m | R³ | Melting point (°C.) or Refractive index ($n_D^{20}$) |
|---|---|---|---|---|
| 85 | H | H | H | 160–162 |
| 86 | F | H | H | |
| 87 | H | H | CH₃ | 190–192 |
| 88 | H | 2-F | H | 131–133 |
| 89 | H | 2-Cl | H | 155–159 |
| 90 | H | 2-Br | H | Not measurable |
| 91 | H | 2-CH₃ | H | |
| 92 | H | 2-C₂H₅ | H | |
| 93 | H | 2-CF₃ | H | 149–154 |
| 94 | H | 2-OCH₃ | H | 163–168 |
| 95 | H | 2-OC₂H₅ | H | |

TABLE 5A-continued

| Compound No. | X | G_m | R³ | Melting point (°C.) or Refractive index ($n_D^{20}$) |
|---|---|---|---|---|
| 96 | H | 2-O-phenyl | H | 1.5972 |
| 97 | H | 2-SCH₃ | H | |
| 98 | H | 2-COCH₃ | H | 152~154 |
| 99 | H | 2-COOC₂H₅ | H | 160~165 |
| 100 | H | 2-NO₂ | H | 130~142 |
| 101 | H | 3-F | H | Not measurable |
| 102 | H | 3-Cl | H | Not measurable |

TABLE 5B

| Compound No. | X | G_m | R³ | Melting point (°C.) or Refractive index ($n_D^{20}$) |
|---|---|---|---|---|
| 103 | F | 3-Cl | H | |
| 104 | H | 3-Br | H | |
| 105 | H | 3-CH₃ | H | 131~135 |
| 106 | H | 3-C₂H₅ | H | |
| 107 | H | 3-CF₃ | H | 168~174 |
| 108 | H | 3-OCH₃ | H | 146~150 |
| 109 | H | 3-OC₂H₅ | H | |
| 110 | H | 3-OCHF₂ | H | |
| 111 | H | 3-O-phenyl | H | Not measurable |
| 112 | H | 3-SCH₃ | H | 154~157 |
| 113 | H | 3-SO₂CH₃ | H | 219~221 |
| 114 | H | 3-N(CH₃)₂ | H | 189~190 |
| 115 | H | 3-COCH₃ | H | 159~161 |
| 116 | H | 3-COOCH₃ | H | |
| 117 | H | 3-COOC₂H₅ | H | 149~153 |
| 118 | H | 3-CN | H | Not measurable |
| 119 | H | 3-NO₂ | H | 174~179 |
| 120 | H | 4-F | H | 175~184 |
| 121 | H | 4-Cl | H | 189~194 |
| 122 | H | 4-CH₃ | H | 168~171 |
| 123 | H | 4-CF₃ | H | 197~205 |
| 124 | H | 4-OCH₃ | H | 164~166 |
| 125 | H | 4-O-phenyl | H | 185~188 |
| 126 | H | 4-SCH₃ | H | 185~190 |

TABLE 5C

| Compound No. | X | G_m | R³ | Melting point (°C.) or Refractive index ($n_D^{20}$) |
|---|---|---|---|---|
| 127 | H | 4-SO₂CH₃ | H | 188~190 |
| 128 | H | 4-N(CH₃)₂ | H | 198~201 |
| 129 | H | 4-COCH₃ | H | 190~194 |
| 130 | H | 4-COOC₂H₅ | H | 145~149 |
| 131 | H | 4-CN | H | 139~141 |

TABLE 5C-continued

| Compound No. | X | $G_m$ | $R^3$ | Melting point (°C.) or Refractive index ($n_D^{20}$) |
|---|---|---|---|---|
| 132 | H | 4-$NO_2$ | H | 206~210 |
| 133 | H | 2,3-$F_2$ | H | |
| 134 | H | 2,3-$Cl_2$ | H | 148~150 |
| 135 | H | 2,4-$Cl_2$ | H | 133~137 |
| 136 | H | 2,5-$F_2$ | H | 186~189 |
| 137 | H | 2,5-$Cl_2$ | H | 146~148 |
| 138 | F | 2,5-$Cl_2$ | H | |
| 139 | Cl | 2,5-$Cl_2$ | H | |
| 140 | H | 2-F, 5-Cl | H | 157~160 |
| 141 | F | 2-F, 5-Cl | H | |
| 142 | H | 2-F, 5-Br | H | |
| 143 | H | 2-F, 5-$NO_2$ | H | Not measurable |
| 144 | F | 2-F, 5-$NO_2$ | H | |
| 145 | H | 2-Cl, 5-F | H | |
| 146 | H | 2-Cl, 5-$NO_2$ | H | |
| 147 | H | 2-$NO_2$, 5-Cl | H | 195~198 |
| 148 | H | 2,6-$Cl_2$ | H | 58~65 |
| 149 | H | 3,4-$F_2$ | H | 167~169 |
| 150 | H | 3,4-$Cl_2$ | H | 161~163 |

TABLE 5D

| Compound No. | X | $G_m$ | $R^3$ | Melting point (°C.) or Refractive index ($n_D^{20}$) |
|---|---|---|---|---|
| 151 | H | 3,4-$(OCH_3)_2$ | H | 150~152 |
| 152 | H | 3,4-(—$OCH_2O$—) | H | 172~173 |
| 153 | H | 3,5-$F_2$ | H | 183~184 |
| 154 | H | 3,5-$Cl_2$ | H | 163~166 |
| 155 | F | 3,5-$Cl_2$ | H | Not measurable |
| 156 | Cl | 3,5-$Cl_2$ | H | Not measurable |
| 157 | H | 3,5-$Cl_2$ | $CH_3$ | 144~146 |
| 158 | H | 3,5-$(CH_3)_2$ | H | |
| 159 | H | 3,5-$(CF_3)_2$ | H | Not measurable |
| 160 | H | 3,5-$(OCH_3)_2$ | H | 169~170 |
| 161 | H | 3,5-$(OCHF_2)_2$ | H | |
| 162 | H | 3,5-$(NO_2)_2$ | H | 215~218 |
| 163 | H | 3-F, 5-Cl | H | |
| 164 | H | 3-F, 5-$NO_2$ | H | |
| 165 | H | 3-Cl, 5-$NO_2$ | H | Not measurable |
| 166 | H | 2,3,5-$Cl_3$ | H | 122~125 |
| 167 | H | 2,4,6-$F_3$ | H | Not measurable |
| 168 | H | 2-$NO_2$, 4,5-$Cl_2$ | H | 187~188 |
| 169 | H | 3,4,5-$Cl_3$ | H | 209~212 |
| 170 | H | 3,5-$Cl_2$, 4-F | H | 146~147 |
| 171 | H | 3,5-$Cl_2$, 4-$CH_3$ | H | 230~232 |
| 172 | H | 3,5-$Cl_2$, 4-$OCH_3$ | H | 165~167 |
| 173 | F | 3,5-$Cl_2$, 4-$OCH_3$ | H | |
| 174 | Cl | 3,5-$Cl_2$, 4-$OCH_3$ | H | |
| 175 | H | 3,5-$Cl_2$, 4-$OCHF_2$ | H | 203~206 |
| 176 | H | 3,5-$Cl_2$, 4-OH | H | 141~145 |
| 177 | H | 3,4,5-$(OCH_3)_3$ | H | 172~174 |
| 178 | H | 2,4-$F_2$, 3,5-$Cl_2$ | H | Not measurable |
| 179 | H | 2,3,5,6-$F_4$ | H | Not measurable |
| 180 | H | 2,3,4,5,6-$F_5$ | H | 179~182 |

Now, the processes for producing the compounds of the present invention will be described in detail with reference to Examples. However, it should be understood that the present invention is by no means restricted by such specific Examples.

EXAMPLE 1

Preparation of ethyl 2-(4-methyl-2-oxo-3-phenyl-3-pyrrolin-1-yl)isobutyrate (Compound No. 47)

325.5 g (1.07 mol) of ethyl 2-[N-(2-oxopropyl)-phenylacetylamino]isobutyrate was dissolved in 1.5 l of ethanol, and 77 g (1.28 mol) of 90% sodium methylate powder was added thereto. The mixture was refluxed under heating for 30 minutes. Ethanol was distilled off, and the residue was poured into ice water. Precipitated crystals were collected by filtration. The crystals were thoroughly washed with hexane and dried to obtain 73 g (yield: 24%) of the desired product having a melting point of from 64 to 66° C.

$^1$H—NMR($CDCl_3$)δ:1.3(t,3H), 1.6(s,6H), 2.2(s,3H), 4.0(s,2H), 4.2(q,2H)

EXAMPLE 2

Preparation of allyl 2-(4-methyl-2-oxo-3-phenyl-3-pyrrolin-1-yl)isobutyrate (Compound No. 54)

1.5 g (5.8 mmol) of 2-(4-methyl-2-oxo-3-phenyl-3-pyrrolin-1-yl)isobutyric acid was dissolved in 50 ml of acetonitrile, and 0.83 g (6 mmol) of potassium carbonate and 0.73 g (6 mmol) of allyl bromide were added thereto. The mixture was refluxed under heating for 1 hour. After completion of the reaction, acetonitrile was distilled off, and ice water was added to the residue. The mixture was extracted with ethyl acetate. The extract was treated by a conventional method to obtain 1.7 g of a crude product. This crude product was purified by column chromatography to obtain 1.4 g (yield: 82%) of the desired product having a melting point of from 65° to 67° C.

$^1$H—NMR($CDCl_3$)δ: 1.6(s,6H), 2.1(s,3H), 3.9(s,2H), 4.5–4.7(m,2H), 5.0–5.4(m,2H), 5.5–6.2(m,1H), 7.1–7.5(m,5H)

EXAMPLE 3

Preparation of N-(1,1-dimethylethyl) 2-(4-methyl-2-oxo-3-phenyl-3-pyrrolin-1-yl)isobutylamide (Compound No. 72)

3.0 g (11.6 mmol) of 2-(4-methyl-2-oxo-3-phenyl-3-pyrrolin-1-yl)isobutyric acid was dissolved in 20 ml of tetrahydrofuran, and 2.3 g (13.9 mmol) of carbonyl diimidazole (CDI) was added thereto. The mixture was stirred at room temperature for 30 minutes. Further, 1.1 g (15.1 mmol) of t-butylamine was added thereto, and the mixture was stirred at 60° C. for 5 hours. After completion of the reaction, the reaction solution was poured into water and extracted with ethyl acetate. The organic layer was washed with water, dried over anhydrous magnesium sulfate and then concentrated to obtain a crude product. This crude product was washed with diethyl ether to obtain 2.6 g (yield: 71%) of the desired product having a melting point of from 137° to 140° C.

$^1$H—NMR($CDCl_3$)δ: 1.3(s,9H), 1.9(s,6H), 2.1(s,3H), 3.9(s,2H), 6.5(bs,1H), 7.1–7.5(m,5H)

EXAMPLE 4

Preparation of N-(2,5-dichlorophenyl) 2-(4-methyl-2-oxo-phenyl-3-pyrrolin-1-yl)isobutylamide (Compound No. 137)

1.50 g (5.79 mmol) of 2-(4-methyl-2-oxo-3-phenyl-3-pyrrolin-1-yl)isobutyric acid was suspended in 20 ml of a carbon tetrachloride-dichloromethane (1:1) solution, and 2.0 g (7.53 mmol) of triphenylphosphine (TPP) was added thereto. The mixture was refluxed under heating for 30 minutes. Then, the reaction solution was cooled with ice, and 0.94 g (5.79 mmol) of 2,5-dichloroaniline and 0.58 g (5.79 mmol) of triethylamine were added thereto. The mixture was stirred at room temperature for 30 minutes. After completion of the reaction, insoluble material was filtered off, and the filtrate was concentrated to some extent and purified by silica gel column chromatography to obtain 1.61 g (yield: 69%) of the desired product having a melting point of from 146° to 148° C.

$^1$H—NMR(CDCl$_3$)δ: 1.7(s,6H), 2.2(s,3H), 4.1(s,2H), 6.8–7.5(m,7H), 8.4(d,1H), 8.8(bs,1H)

EXAMPLE 5

Preparation of N-(3-methylsulfonylphenyl) 2-(4-methyl-2-oxo-3-phenyl-3-pyrrolin-1-yl) isobutylamide (Compound No. 113)

1.50 g (3.95 mmol) of N-(3-methylthiophenyl) 2-(4-methyl-2-oxo-3-phenyl-3-pyrrolin-1-yl)isobutylamide was dissolved in 10 ml of methanol, and 3.64 g (5.92 mmol) of OXONE (trademark) was added thereto. Then, 10 ml of water was gradually added thereto under stirring so that the liquid temperature would not exceed 40° C., and then the mixture was stirred at room temperature for two hours. After completion of the reaction, the reaction solution was extracted with chloroform, washed with an aqueous sodium hydrogencarbonate solution and then with water, dried over anhydrous magnesium sulfate and then concentrated to dryness. The solid thereby obtained was washed with diethyl ether to obtain 1.33 g (yield: 82%) of the desired product having a melting point of from 219° to 221° C.

$^1$H—NMR(CDCl$_3$)δ: 1.7(s,6H), 2.1(s,3H), 3.0(s,2H), 7.1–8.0(m,9H), 9.5(bs,1H)

EXAMPLE 6

Preparation of N-(3,5-dichloro-4-methoxyphenyl) 2-(4-methyl-2-oxo-3-phenyl-3-pyrrolin-1-yl) isobutylamide (Compound No. 172)

1.50 g (3.58 mmol) of N-(3,5-dichloro-4-hydroxyphenyl) 2-(4-methyl-2-oxo-3-phenyl-3-pyrrolin-1-yl)isobutylamide was dissolved in 10 ml of acetonitrile, and 0.76 g (5.37 mmol) of methyl iodide and 0.64 g (4.65 mmol) of potassium carbonate were added thereto. The mixture was reacted at room temperature for 3 hours. After completion of the reaction, the reaction solution was poured into water and extracted with ethyl acetate. The ethyl acetate solution was washed with water, then dried over anhydrous magnesium sulfate and concentrated to dryness. The solid thereby obtained was washed with isopropyl ether to obtain 0.93 g (yield: 60%) of the desired product having a melting point of from 165° to 167° C.

$^1$H—NMR(CDCl$_3$)δ: 1.7(s,6H), 1.2(s,3H), 3.8(s,3H), 4.0(s,2H), 7.2–7.5(m,7H), 9.5(bs,1H)

EXAMPLE 7

Preparation of N-benzenesulfonyl 2-(4-methyl-2-oxo-3-phenyl-3-pyrrolin-1-yl)isobutylamide (Compound No. 75)

1.2 g (7.7 mmol) of benzenesulfone amide was added to a DMF suspension of 0.37 g (9.2 mmol) of 60% sodium hydride, and the mixture was stirred at room temperature for one hour. On the other hand, 2.0 g (7.7 mmol) of 2-(4-methyl-2-oxo-3-phenyl-3-pyrrolin-1-yl)isobutyric acid was dissolved in 20 ml of tetrahydrofuran, and 1.37 g (8.4 mmol) of carbonyl diimidazole (CDI) was added thereto. The mixture was stirred for one hour. This reaction solution was dropwise added to the previously prepared solution of the sodium salt of benzenesulfone amide at room temperature, and the mixture was stirred for two hours. After completion of the reaction, the reaction solution was poured into ice water and adjusted to pH3 with hydrochloric acid. This solution was extracted with ethyl acetate, and the extract was treated by a conventional method to obtain 2.1 g (yield: 70%) of the desired product having a melting point of from 168 to 171° C.

$^1$H—NMR(CDCl$_3$)δ: 1.5(s,6H), 2.2(s,3H), 3.0(s,2H), 7.2–7.6(m,7H), 11.0(bs,H)

EXAMPLE 8

Preparation of 1-[1-(3-chlorobenzoyl)-1-methylethyl]-4-methyl-3-phenyl-3-pyrrolin-2-one) (Compound No. 7)

A solution of 3.7 g (17 mmol) of 3-chlorophenyl magnesium bromide in 20 ml of tetrahydrofuran was dropwise added at room temperature under a nitrogen stream to a solution of 2 g (7 mmol) of ethyl 2-(4-methyl-2-oxo-3-phenyl-3-pyrrolin-1-yl) isobutyrate in 20 ml of tetrahydrofuran. The mixture was stirred for one day at room temperature. Then, the reaction solution was poured into ice water containing ammonium chloride and extracted with ethyl acetate. The extract was treated by a conventional method to obtain a crude product. The crude product was purified by column chromatography to obtain 0.7 g (yield: 28%) of the desired product having a melting point of from 134° to 138° C.

$^1$H—NMR(CDCl$_3$)δ: 1.6(s,6H), 2.2(s,3H), 4.1(s,2H), 7.0–7.8(m,9H)

EXAMPLE 9

Preparation of 1-[2-(3,5-dichlorophenyl)-1,1-dimethyl-2-oxoethyl]-4-methyl-3-phenyl-3-pyrrolin-2-one (Compound No. 24)

A solution of 2.2 g (27.6 mmol) of dimethyl sulfoxide in 10 ml of dichloromethane was dropwise added over a period of 15 minutes at −60° C. to a solution of 2.65 g (20.8 mmol) of oxalyl dichloride in 40 ml of dichloromethane. A few minutes later, a solution of 5.4 g (13.8 mmol) of 1-[2-hydroxy-1,1-dimethyl-2-(3,5-dichlorophenyl)ethyl]-4-methyl-3-phenyl-3-pyrrolin-2-one in 20 ml of dichloromethane was dropwise added thereto at −60° C. The mixture was stirred at the same temperature for further 30 minutes. Then, 7 g (69 mmol) of triethylamine was dropwise added thereto, and the mixture was stirred at −60° C. for further 15 minutes. The reaction solution was restored to room temperature, and 20 ml of water was added thereto. The mixture was thoroughly stirred. The organic layer was treated by a conventional method, and crystals thereby obtained were washed with isopropyl ether to obtain 4.6 g (yield: 87%) of the desired product having a melting point of from 157° to 160° C.

$^1$H—NMR(CDCl$_3$)δ: 1.6(s,6H), 2.2(s,3H), 4.1(s,2H), 7.0–7.3(m,6H), 7.6(s,1H), 7.7(s,1H)

EXAMPLE 10

Preparation of 1-(1,1-dimethyl-2-oxohexyl)-4-methyl-3-phenyl-3-pyrrolin-2-one (Compound No. 38)

5 g (19.3 mmol) of 2-(4-methyl-2-oxo-3-phenyl-3-pyrrolin-1-yl)isobutyric acid was dissolved in 50 ml of tetrahydrofuran, and a solution of 41 g (97 mmol) of 15% n-butyl lithium in n-hexane was dropwise added at 0° C. under a nitrogen stream. After completion of the dropwise addition, the mixture was stirred at room temperature for one day. The reaction solution was poured into ice water and extracted with ethyl acetate. The extract was treated by a conventional method, and the crude product thereby obtained was purified by column chromatography to obtain 2.7 g (yield: 47%) of the desired product having a melting point of from 87° to 89° C.

$^1$H—NMR(CDCl$_3$)δ: 0.7–1.7(m,13H), 2.2(s,3H), 2.5(t,2H), 4.0(s,2H), 7.2–7.6(m,5H)

EXAMPLE 11

Preparation of 1-[2-(3,5-dichlorophenyl)-2-hydroxyimino-1,1-dimethylethyl]-4-methyl-3-phenyl -3-pyrrolin-2-one (Compound No. 25)

1.0 g (2.6 mmol) of 1-[2-(3,5-dichlorophenyl)-1,1-dimethyl-2-oxoethyl]-4-methyl-phenyl -3-pyrrolin-2-one was dissolved in 30 ml of ethanol, and 0.66 g (9.3 mmol) of hydroxyamine hydrochloride, 1.14 g (14.1 mmol) of sodium acetate and 2 ml of water were added thereto. The mixture was refluxed under heating for two days. After concentration, ice water was added thereto, and precipitated crystals were collected by filtration. The crystals were recrystallized from ethanol to obtain 0.6 g (yield: 60%) of the desired product having a melting point of from 266° to 268° C.

$^1$H—NMR(CDCl$_3$)δ: 1.7(s,6H),2.1(s,3H), 3.9(s,2H), 7.0–7.5m,9H)

Now, processes for producing starting material compounds will be described with reference to Reference Examples.

REFERENCE EXAMPLE 1

Preparation of ethyl 2-(2-oxopropylamino)isobutyrate 430 g (2.56 mol) of ethyl 2-aminoisobutyrate hydrochloride was dissolved in 2 l of DMAc, and 652 g (6.46 mol) of triethylamine and 373 g (4.03 mol) of chloroacetone were added thereto. The mixture was stirred and reacted under nitrogen stream at 80° C. for 3 hours. After completion of the reaction, the reaction solution was poured into 20 l of ice water and extracted twice with 2 l of ethyl acetate. The extracted solution was treated by a conventional method to obtain 402 g (yield: 84%) of the desired product.

$^1$H—NMR(CDCl$_3$)δ: 1.25(t,3H), 1.3(s,6H), 2.1(s,3H), 2.5(bs,1H), 3.5(s,2H), 4.1(q,2H)

REFERENCE EXAMPLE 2

Preparation of ethyl 2-[N-(2-oxopropyl)phenylacetylamino]isobutyrate 402 g (2.15 mol) of ethyl 2-(2-oxopropylamino)isobutyrate obtained in Reference Example 1, was dissolved in 1.5 l of acetone. Then, 238 g (2.36 mol) of triethylamine was added thereto. To this solution, 365 g (2.36 mol) of phenylacetyl chloride was dropwise added under cooling with ice. After completion of the dropwise addition, the mixture was stirred for one day at room temperature. The precipitated salt was removed by filtration, and the filtrate was concentrated. The residue was dissolved in 2 l of ethyl acetate, thoroughly washed with water and treated by a conventional method to obtain 651 g (yield: 99%) of the desired product.

$^1$H—NMR(CDCl$_3$)δ: 1.2(t,3H), 1.4(s,6H), 2.1(s,3H), 3.5(s,2H), 4.1(q,2H), 4.1(s,2H), 7.2(bs,5H

REFERENCE EXAMPLE 3

Preparation of 2-methyl-2-(4-methyl-2-oxo-3-phenyl-3-pyrrolin-1-yl)propanol 52.4 g (200 mmol) of ethyl 2-(4-methyl-2-oxo-3-phenyl-3-pyrrolin-1-yl)isobutyrate was dissolved in 300 ml of tetrahydrofuran, and the solution was cooled to −30° C. In a dropping funnel, 7.6 g (200 mmol) of lithium alminum hydride was suspended in 100 ml of tetrahydrofuran, and the suspension was dropwise added at −30° C. After completion of the dropwise addition, the cooling medium was removed, and a suitable amount of water was added, and excess of lithium aluminum hydride was quenched. Insoluble material was removed by filtration, and the filtrate was concentrated and the solid thus obtained was washed with isoproyl ether to obtain 40.9 g (yield: 83%) of the desired product having a melting point of from 77° to 78° C.

$^1$H—NMR(CDCl$_3$)δ: 1.4(s,6H), 2.1(s,3H), 3.8(sb,2H) , 3.9(s,2H), 5.4(sb,1H), 7.2–7.4(m,5H)

REFERENCE EXAMPLE 4

Preparation of 2-(4-methyl-2-oxo-3-phenyl-3-pyrrolin-1-yl)isobutylaldehyde 39 g (500 mmol) of dimethyl sulfoxide was dissolved in 500 ml of dichloromethane, and the solution was cooled to −60° C. Then, 31.7 g (250 mmol) of oxalyl dichloride was dropwise added thereto. After the dropwise addition, the mixture was stirred for 10 minutes. Then, a solution of 40.9 g (167 mmol) of 2-methyl-2-(4-methyl-2-oxo-3-phenyl-3-pyrrolin-1-yl)propanol in 300 ml of dichloromethane was dropwise added thereto at −60° C. After the dropwise addition, the mixture was stirred for 30 minutes, and 84 g (833 mmol) of triethylamine was dropwise added at the same temperature. The cooling medium was removed, and the solution was stirred at room temperature for one hour. The reaction solution was poured into water, and the organic layer was washed twice with water, then dried over anhydrous magnesium sulfate, concentrated and washed with a solvent mixture of diethyl ether-ethanol to obtain 39.4 g (yield: 97%) of the desired product having a melting point of from 116° to 119° C.

$^1$H—NMR(CDCl$_3$)δ: 1.4(s,6H), 2.2(s,3H), 3.9(s,2H), 7.2–7.5(m,5H) , 9.5(s,1H)

REFERENCE EXAMPLE 5

Preparation of 1-[2-hydroxy-1,1-dimethyl-2-(3,5-dichlorophenyl)ethyl]-4-methyl-3-phenyl -3-pyrrolin-2-one (Intermediate No. 11)

A solution of 10 g (40 mmol) of 3,5-dichlorophenylmagnesium bromide in 30 ml of tetrahydrofuran was gradually dropwise added at room temperature under a nitrogen stream to a solution of 5 g (20 mmol) of 2-(4-methyl-2-oxo-3-phenyl-3-pyrrolin-1-yl)isobutylaldehyde in 20 ml of tetrahydrofuran. The mixture was stirred at room temperature for 3 hours. The reaction solution was poured into ice water containing ammonium chloride and extracted with ethyl acetate. The extract was treated by a conventional method to obtain crude crystals. The crude crystals were thoroughly washed with isopropyl ether to obtain 6 g (yield: 77%) of the desired product having a melting point of from 171° to 173° C.

$^1$H—NMR(CDCl$_3$)δ: 1.4(s,3H), 1.6(s,3H), 2.0(s,3H), 3.6(q,2H), 4.8(bd,1H), 6.4(bd,1H), 7.2(bs,3H), 7.4(bs,5H)

The herbicidal composition of the present invention contains one or more 2-oxo-3-pyrroline derivatives of the formula (I) as an active ingredient.

The compound of the present invention can be used as it is as a herbicide, but it may be used in such an appropriate formulation as a dust, a wettable powder, an emulsifiable concentrate, a micro-particle agent or a granule agent by blending it with a carrier, a surfactant, a dispersing agent or an adjuvant which may be commonly used in the formulation of agricultural chemicals.

As a carrier to be used for these formulations, there may be enumerated a solid carrier such as Jeeklite, talc, bentonite, clay, kaolin, diatomaceous earth, white carbon, vemiculite, calcium carbonate, slaked lime, silica sand, ammonium sulfate or urea, or a liquid carrier such as 2-propanol, xylene, cyclohexanone or methyl naphthalene.

As a surfactant and a dispersing agent, there may be enumerated, for example, a metal salt of an alkylbenzenesulfonic acid, a metal salt of a dinaphthylmethanedisulfonic acid, an alcohol-sulfuric acid ester, an alkylaryl sulfonate, a lignin sulfonate, a polyoxyethylene glycol ether, a polyoxyethylene alkyl aryl ether or a polyoxyethylene sorbitol monoalkylate. As an adjuvant, for example, carboxymethyl cellulose, polyethylene glycol or gum arabic may be enumerated.

The proportion of the active ingredient is optionally selected depending on its use, and it is usually from 0.01 to 10% by weight, preferably from 0.05 to 5% by weight, in the cases of dust and granule formulations, and from 1 to 50% by weight, preferably from 5 to 30% by weight, in the cases of emulsifiable concentrate and wettable powder formulations.

In practical use, the herbicide of the present invention may be diluted to a suitable concentration before applying it or may be directly applied. The amount of the herbicide of the present invention may be optionally varied depending on the type of the compound used, the type of weed to be controlled, growing tendency, environmental conditions and the type of formulation used. When the herbicide of the present invention is directly applied as in the case of powder or granule formulation, it is used at a dose of from 0.1 g to 5 kg, preferably from 1 g to 1 kg of the active ingredient per 10 ares. In the case of liquid application such as an emulsifiable concentrate or wettable powder formulation, the active ingredient may optionally be diluted to a concentration of from 0.1 to 50,000 ppm, preferably from 10 to 10,000 ppm for application.

The herbicide of the present invention may be applied to foliage, soil or water surface.

If desired, the compound of the present invention may be used in combination with insecticides, sterilizers, other herbicides, plant growth controlling agents, fertilizers or the like.

Now, typical Formulation Examples for the herbicidal composition of the present invention will be given. The types of compounds and additives and the blending ratios are not limited thereto, and may optionally be varied in wide ranges. In these Examples, "part" means "part by weight".

FORMULATION EXAMPLE 1

Wettable Powder

10 Parts of Compound No. 7, 0.5 part of polyoxyethyleneoctylphenyl ether, 0.5 part of sodium β-naphthalenesulfonate-formalin condensate, 20 parts of diatomaceous earth and 69 parts of clay were mixed and pulverized to obtain a wettable powder.

FORMULATION EXAMPLE 2

Wettable Powder

10 Parts of Compound No. 6, 0.5 part of polyoxyethyleneoctylphenyl ether, 0.5 part of sodium β-naphthalenesulfonate-formalin condensate, 20 parts of diatomaceous earth, 5 parts of white carbon and 64 parts of clay were mixed and pulverized to obtain a wettable powder.

FORMULATION EXAMPLE 3

Wettable Powder

10 Parts of Compound No. 1, 0.5 part of sodium β-naphthalenesulfonate-formalin condensate, 0.5 part of sodium lauryl sulfate, 20 parts of diatomaceous earth, 5 parts of white carbon and 64 parts of calcium carbonate were mixed and pulverized to obtain a wettable powder.

FORMULATION EXAMPLE 4

Emulsifiable Concentrate

10 Parts of Compound No. 37, 80 parts of equivalent amount mixture of xylene and isophorone, and 10 parts of a surfactant mixture of polyoxyethylene sorbitol alkylate, polyoxyethylenealkylaryl polymer and alkylaryl sulfonate were thoroughly stirred to obtain an emulsifiable concentrate.

FORMULATION EXAMPLE 5

Granule

3 Parts of Compound No. 24, 87 parts of a bulking agent comprising a 1:3 mixture of talc and bentonite, 5 parts of white carbon, 5 parts of a surfactant mixture of polyoxyethylenesorbitol alkylate, polyoxyethylenealkylaryl polymer and alkylarylsulfonate and 10 parts of water were thoroughly kneaded to obtain a paste-like material. The paste-like material was then extruded through a sieve aperture of 0.7 mm in diameter, and the extruded product was dried and cut into pieces of 0.5 to 1 mm in length to obtain granules.

Now, the herbicidal effects of the compounds of the present invention will be described with reference to the following Test Examples.

TEST EXAMPLE 1

Herbicidal Effect Test by Paddy Field Soil Treatment

In a plastic pot (surface area: 100 cm$^2$) filled with paddy field soil, barnyardgrass (Ec), monochoria (Mo) and bulrush (Sc) were sown after puddling and leveling, and flooded to a water depth of 3 cm. Next day, a wettable powder prepared in accordance with Formulation Example 1 was diluted with water, and was applied dropwise to the water surface in such manner as to apply 100 g of the active ingredient per 10 ares. The plants were then cultured in a green house, and the evaluation of the herbicidal effect was conducted on the 21st day after the treatment in accordance with the standards as identified in Table 6. The results are shown in Tables 7A, 7B and 7C.

TEST EXAMPLE 2

Herbicidal Effect Test by Upland Field Soil Treatment

In a plastic pot (surface area: 120 cm$^2$) filled with upland field soil, barnyardgrass (Ec), crabgrass (Di), slender amaranth (Am), and rice flatsedge (Ci) were sown and covered with soil. A wettable powder prepared in accordance with Formulation Example 1 was diluted with water, and applied uniformly to the soil surface by a small-sized sprayer in an amount of 100 l/10 ares so as to apply 100 g of the active ingredient per 10 ares. The plants were then cultured in a green house, and the evaluation of the herbicidal effect was conducted on the 21th day after the treatment in accordance with the standards as identified in Table 6. The results are shown in Table 8A.

TEST EXAMPLE 3

Herbicidal Effect Test by Upland Field Soil Treatment

In a plastic pot (surface area: 120 cm$^2$) filled with upland field soil, barnyardgrass (Ec), crabgrass (Di), slender amaranth (Am), common lambsquarters (Ch) and rice flatsedge (Ci) were sown and covered with soil. A wettable powder prepared in accordance with Formulation Example 1 was diluted with water, and applied uniformly to the soil surface by a small-sized sprayer in an amount of 100 l/10 ares so as to apply 100 g of the active ingredient per 10 ares. The plants were then cultured in the green house, and the evaluation of the herbicidal effect was conducted on the 21st day after the treatment. The results are shown in Tables 8B and 8C.

TEST EXAMPLE 4

Crop Plant Selectivity Test by Paddy Field Soil Treatment

Into a plastic pot of a 1/10,000 are size, paddy field soil was filled, irrigated, puddled and leveled. Then, barnyardgrass (Ec), monochoria (Mo) and bulrush (Sc) were sown in a depth of 0.5 cm. Further, two seedlings of rice (Or) of 2.5 leaf stage were transplanted in a depth of 2 cm. Water was introduced to a water depth of 3 cm. Next day, a wettable powder prepared in accordance with Formulation Example 1 was diluted with water, and was dropwise applied to the water surface. The plants were then cultured in a green house, and the herbicidal effect and phytotoxicity were evaluated on the 28th day after the treatment in accordance with the standards as identified in Table 6. The results are shown in Tables 9A, 9B and 9C.

TEST EXAMPLE 5

Crop Plant Selectivity Test by Upland Field Soil Treatment

In a plastic pot (surface area: 600 cm$^2$) filled with upland field soil, soybean (Gl), cotton (Go), barnyardgrass (Ec), crabgrass (Di), green foxtail (Se), johnsongrass (So) and slender amaranth (Am) were sown and covered with soil. Next day, a wettable powder prepared in accordance with Formulation Example 1 was diluted with water in a predetermined amount and applied uniformly on the soil surface by a small-sized sprayer in an amount of 100 l/10 ares. The plants were then cultured in a green house, and the herbicidal effects were evaluated on the 21st day after the treatment in accordance with the standards as identified in Table 6. The test results are shown in Table 10.

Further, as a comparative compound, 1-(2-chloro-α,α-dimethylbenzyl-4-methyl-3-phenyl-3-pyrrolin-2-one (Compound disclosed in U.S. Pat. No. 5,006,157) was used.

TABLE 6

| Index No. | Herbicidal effects and phytotoxicity |
| --- | --- |
| 5 | Herbicidal effect: at least 90% |
|   | Phytotoxicity: at least 90% |
| 4 | Herbicidal effect: at least 70% and less than 90% |
|   | Phytotoxicity: at lest 70% and less than 90% |
| 3 | Herbicidal effect: at least 50% and less than 70% |
|   | Phytotoxicity: at least 50% and less than 70% |
| 2 | Herbicidal effect: at least 30% and less than 50% |
|   | Phytotoxicity: at least 30% and less than 50% |
| 1 | Herbicidal effect: at least 10% and less than 30% |
|   | Phytotoxicity: at least 10% and less than 30% |
| 0 | Herbicidal effect: 0 to less than 10% |
|   | Phytotoxicity: 0 to less than 10% |

TABLE 7A

| Compound No. | Herbicidal effect | | | Compound No. | Herbicidal effect | | |
| --- | --- | --- | --- | --- | --- | --- | --- |
|  | Ec | Mo | Sc |  | Ec | Mo | Sc |
| 1 | 5 | 5 | 5 | 24 | 5 | 5 | 5 |
| 3 | 5 | 5 | 5 | 32 | 5 | 5 | 5 |
| 4 | 5 | 5 | 5 | 33 | 5 | 5 | 5 |
| 5 | 5 | 4 | 5 | 34 | 5 | 5 | 5 |
| 6 | 5 | 5 | 5 | 35 | 5 | 5 | 5 |
| 7 | 5 | 5 | 5 | 36 | 5 | 5 | 5 |
| 10 | 5 | 5 | 5 | 37 | 5 | 5 | 5 |
| 14 | 5 | 5 | 5 | 38 | 5 | 5 | 5 |
| 16 | 5 | 5 | 5 | 39 | 5 | 5 | 5 |
| 17 | 5 | 4 | 5 | 40 | 5 | 5 | 5 |
| 18 | 5 | 5 | 5 | 41 | 5 | 5 | 5 |
| 19 | 5 | 5 | 5 | 42 | 5 | 5 | 5 |
| 22 | 5 | 5 | 5 | 43 | 5 | 4 | 5 |
| 23 | 5 | 5 | 5 | 44 | 5 | 4 | 5 |

TABLE 7B

| Compound No. | Herbicidal effect | | | Compound No. | Herbicidal effect | | |
| --- | --- | --- | --- | --- | --- | --- | --- |
|  | Ec | Mo | Sc |  | Ec | Mo | Sc |
| 46 | 5 | 5 | 5 | 99 | 5 | 5 | 5 |
| 47 | 5 | 5 | 5 | 100 | 5 | 5 | 5 |
| 48 | 5 | 5 | 5 | 101 | 5 | 5 | 5 |
| 49 | 5 | 5 | 5 | 102 | 5 | 5 | 5 |
| 50 | 5 | 5 | 5 | 105 | 5 | 5 | 5 |
| 54 | 5 | 5 | 5 | 107 | 5 | 5 | 5 |
| 55 | 5 | 5 | 5 | 108 | 5 | 5 | 5 |
| 58 | 5 | 5 | 5 | 111 | 5 | 5 | 5 |
| 59 | 5 | 5 | 5 | 112 | 5 | 5 | 5 |
| 68 | 5 | 5 | 3 | 113 | 5 | 5 | 5 |
| 72 | 5 | 5 | 5 | 114 | 4 | 5 | 5 |
| 84 | 5 | 3 | 5 | 115 | 5 | 5 | 5 |
| 85 | 5 | 5 | 5 | 121 | 5 | 5 | 5 |
| 88 | 5 | 5 | 5 | 122 | 5 | 5 | 5 |
| 89 | 5 | 5 | 5 | 123 | 5 | 5 | 5 |
| 91 | 5 | 5 | 5 | 124 | 5 | 5 | 5 |
| 93 | 5 | 5 | 5 | 125 | 5 | 5 | 3 |
| 94 | 5 | 5 | 5 | 126 | 5 | 5 | 5 |
| 98 | 5 | 5 | 5 | 127 | 5 | 5 | 5 |

TABLE 7C

| Compound No. | Herbicidal effect | | | Compound No. | Herbicidal effect | | |
| --- | --- | --- | --- | --- | --- | --- | --- |
|  | Ec | Mo | Sc |  | Ec | Mo | Sc |
| 129 | 5 | 5 | 5 | 154 | 5 | 5 | 5 |
| 130 | 5 | 5 | 5 | 155 | 5 | 5 | 5 |
| 131 | 5 | 5 | 5 | 156 | 5 | 5 | 5 |
| 132 | 5 | 5 | 5 | 157 | 5 | 5 | 3 |
| 134 | 5 | 5 | 5 | 159 | 5 | 5 | 3 |
| 135 | 5 | 5 | 5 | 160 | 5 | 5 | 5 |
| 136 | 5 | 5 | 5 | 162 | 5 | 5 | 5 |

TABLE 7C-continued

| Compound No. | Herbicidal effect | | | Compound No. | Herbicidal effect | | |
|---|---|---|---|---|---|---|---|
| | Ec | Mo | Sc | | Ec | Mo | Sc |
| 137 | 5 | 5 | 5 | 165 | 5 | 5 | 5 |
| 140 | 5 | 5 | 5 | 166 | 5 | 5 | 5 |
| 143 | 5 | 5 | 5 | 167 | 5 | 5 | 5 |
| 147 | 5 | 5 | 5 | 170 | 5 | 5 | 5 |
| 148 | 5 | 5 | 5 | 172 | 5 | 5 | 5 |
| 149 | 5 | 5 | 5 | 175 | 5 | 5 | 4 |
| 150 | 5 | 5 | 5 | 177 | 5 | 5 | 5 |
| 151 | 5 | 5 | 5 | 178 | 5 | 5 | 5 |
| 152 | 5 | 5 | 5 | 179 | 5 | 5 | 5 |
| 153 | 5 | 5 | 5 | 180 | 5 | 5 | 5 |

TABLE 8A

| Compound No. | Herbicidal effect | | | |
|---|---|---|---|---|
| | Ec | Di | Am | Ci |
| 1 | 5 | 5 | 5 | 5 |
| 6 | 5 | 5 | 3 | 5 |
| 7 | 5 | 5 | 5 | 5 |
| 10 | 5 | 5 | 4 | 5 |
| 16 | 5 | 5 | 4 | 5 |
| 23 | 5 | 5 | 5 | 5 |
| 24 | 5 | 5 | 3 | 5 |
| 33 | 5 | 4 | 4 | 5 |
| 35 | 5 | 5 | 4 | 5 |
| 37 | 5 | 5 | 4 | 5 |
| 38 | 5 | 5 | 5 | 5 |
| 41 | 5 | 5 | 4 | 5 |

TABLE 8B

| Compound No. | Herbicidal effect | | | | |
|---|---|---|---|---|---|
| | Ec | Di | Am | Ch | Ci |
| 46 | 5 | 5 | 5 | 5 | 5 |
| 47 | 5 | 5 | 5 | 5 | 5 |
| 48 | 5 | 4 | 5 | 5 | 5 |
| 49 | 5 | 5 | 5 | 5 | 5 |
| 50 | 5 | 4 | 4 | 5 | 5 |
| 54 | 5 | 5 | 5 | 5 | 5 |
| 59 | 5 | 4 | 5 | 5 | 5 |
| 72 | 5 | 5 | 3 | 5 | 5 |
| 85 | 5 | 5 | 5 | 3 | 5 |
| 88 | 5 | 5 | 5 | 5 | 5 |
| 89 | 5 | 5 | 5 | 5 | 5 |
| 93 | 5 | 5 | 5 | 3 | 5 |
| 94 | 5 | 5 | 5 | 3 | 5 |
| 100 | 5 | 5 | 5 | 5 | 5 |
| 101 | 5 | 5 | 5 | 5 | 5 |
| 102 | 5 | 5 | 5 | 4 | 5 |
| 105 | 5 | 5 | 5 | 5 | 5 |
| 107 | 5 | 5 | 5 | 4 | 5 |
| 108 | 5 | 5 | 5 | 4 | 5 |
| 111 | 5 | 5 | 5 | 5 | 5 |
| 112 | 5 | 5 | 4 | 4 | 5 |
| 113 | 5 | 4 | 5 | 4 | 5 |
| 115 | 4 | 5 | 5 | 3 | 5 |
| 117 | 5 | 5 | 5 | 3 | 5 |
| 118 | 5 | 5 | 5 | 5 | 5 |
| 119 | 5 | 5 | 5 | 5 | 5 |
| 120 | 3 | 5 | 5 | 3 | 5 |
| 122 | 5 | 5 | 5 | 5 | 5 |
| 124 | 4 | 5 | 5 | 4 | 5 |

TABLE 8C

| Compound No. | Herbicidal effect | | | | |
|---|---|---|---|---|---|
| | Ec | Di | Am | Ch | Ci |
| 130 | 5 | 5 | 4 | 3 | 5 |
| 131 | 5 | 5 | 5 | 5 | 5 |
| 132 | 3 | 3 | 5 | 5 | 5 |
| 136 | 5 | 5 | 5 | 5 | 5 |
| 137 | 5 | 5 | 5 | 5 | 5 |
| 140 | 5 | 5 | 5 | 5 | 5 |
| 148 | 5 | 5 | 5 | 5 | 5 |
| 149 | 5 | 5 | 5 | 5 | 5 |

TABLE 8C-continued

| Compound No. | Herbicidal effect | | | | |
|---|---|---|---|---|---|
| | Ec | Di | Am | Ch | Ci |
| 150 | 3 | 5 | 5 | 5 | 5 |
| 152 | 5 | 5 | 5 | 5 | 5 |
| 153 | 5 | 5 | 5 | 5 | 5 |
| 154 | 5 | 5 | 5 | 5 | 5 |
| 155 | 5 | 5 | 5 | 5 | 5 |
| 160 | 5 | 5 | 5 | 5 | 5 |
| 170 | 5 | 5 | 5 | 5 | 5 |
| 172 | 5 | 5 | 5 | 5 | 5 |
| 175 | 4 | 5 | 5 | 5 | 5 |
| 178 | 5 | 5 | 4 | 4 | 5 |
| 179 | 5 | 5 | 5 | 5 | 5 |

TABLE 9A

| Compound No. | Dose of active ingredient (g/10a) | Herbicidal effect | | | Phytotoxicity Or |
|---|---|---|---|---|---|
| | | Ec | Mo | Sc | |
| 1 | 25.0 | 5 | 5 | 5 | 1 |
| 3 | 25.0 | 5 | 5 | 5 | 0 |
| 4 | 25.0 | 5 | 5 | 5 | 0 |
| 5 | 25.0 | 5 | 2 | 5 | 0 |
| 6 | 25.0 | 5 | 5 | 5 | 1 |
| 7 | 25.0 | 5 | 5 | 5 | 0 |
| 10 | 25.0 | 5 | 5 | 5 | 0 |
| 14 | 25.0 | 5 | 5 | 5 | 0 |
| 16 | 25.0 | 5 | 5 | 5 | 0 |
| 17 | 25.0 | 5 | 4 | 5 | 1 |
| 18 | 25.0 | 5 | 5 | 5 | 0 |
| 19 | 25.0 | 5 | 5 | 5 | 0 |
| 22 | 25.0 | 5 | 4 | 5 | 0 |
| 23 | 6.3 | 5 | 5 | 5 | 0 |
| 24 | 25.0 | 5 | 5 | 5 | 0 |
| 33 | 25.0 | 5 | 5 | 5 | 2 |
| 34 | 25.0 | 5 | 5 | 5 | 0 |
| 35 | 25.0 | 5 | 5 | 5 | 0 |
| 37 | 25.0 | 5 | 5 | 5 | 0 |
| 38 | 25.0 | 5 | 5 | 5 | 0 |
| 39 | 25.0 | 5 | 5 | 5 | 0 |
| 40 | 25.0 | 5 | 5 | 5 | 0 |
| 41 | 25.0 | 5 | 5 | 5 | 0 |
| 42 | 25.0 | 5 | 5 | 5 | 0 |
| 43 | 25.0 | 5 | 4 | 5 | 0 |
| 44 | 25.0 | 5 | 2 | 5 | 0 |

TABLE 9B

| Compound No. | Dose of active ingredient (g/10a) | Herbicidal effect | | | Phytotoxicity Or |
|---|---|---|---|---|---|
| | | Ec | Mo | Sc | |
| 46 | 25.0 | 5 | 5 | 5 | 0 |
| 47 | 25.0 | 5 | 5 | 5 | 0 |
| 48 | 25.0 | 5 | 5 | 5 | 0 |
| 49 | 25.0 | 5 | 5 | 5 | 0 |
| 50 | 25.0 | 5 | 5 | 5 | 0 |
| 54 | 25.0 | 5 | 5 | 5 | 1 |
| 55 | 25.0 | 5 | 5 | 5 | 0 |
| 58 | 25.0 | 5 | 5 | 5 | 0 |
| 59 | 25.0 | 5 | 5 | 5 | 0 |
| 68 | 25.0 | 5 | 5 | 5 | 0 |
| 85 | 6.3 | 5 | 5 | 5 | 1 |
| 89 | 25.0 | 5 | 5 | 5 | 0 |
| 91 | 25.0 | 5 | 5 | 5 | 0 |
| 93 | 6.3 | 5 | 5 | 5 | 0 |
| 94 | 25.0 | 5 | 5 | 5 | 0 |
| 98 | 25.0 | 4 | 3 | 5 | 0 |
| 100 | 6.3 | 5 | 4 | 4 | 1 |
| 101 | 25.0 | 5 | 5 | 5 | 1 |
| 102 | 25.0 | 5 | 5 | 5 | 0 |
| 105 | 25.0 | 5 | 5 | 5 | 1 |
| 107 | 6.3 | 5 | 5 | 5 | 1 |
| 111 | 25.0 | 5 | 5 | 4 | 0 |
| 112 | 25.0 | 5 | 5 | 5 | 0 |
| 113 | 25.0 | 5 | 5 | 5 | 0 |
| 115 | 25.0 | 5 | 5 | 5 | 1 |

TABLE 9B-continued

| Compound No. | Dose of active ingredient (g/10a) | Herbicidal effect Ec | Mo | Sc | Phytotoxicity Or |
|---|---|---|---|---|---|
| 117 | 25.0 | 5 | 5 | 5 | 1 |
| 118 | 6.3 | 5 | 5 | 5 | 0 |
| 120 | 6.3 | 5 | 5 | 5 | 0 |
| 121 | 25.0 | 5 | 5 | 5 | 0 |
| 122 | 25.0 | 5 | 5 | 5 | 0 |

TABLE 9C

| Compound No. | Dose of active ingredient (g/10a) | Herbicidal effect Ec | Mo | Sc | Phytotoxicity Or |
|---|---|---|---|---|---|
| 123 | 25.0 | 5 | 5 | 5 | 0 |
| 124 | 25.0 | 5 | 5 | 5 | 0 |
| 129 | 25.0 | 4 | 4 | 5 | 0 |
| 130 | 25.0 | 5 | 5 | 5 | 0 |
| 131 | 6.3 | 5 | 5 | 5 | 0 |
| 132 | 25.0 | 4 | 5 | 5 | 0 |
| 134 | 25.0 | 5 | 4 | 5 | 0 |
| 135 | 25.0 | 5 | 5 | 5 | 0 |
| 137 | 25.0 | 5 | 5 | 5 | 0 |
| 143 | 25.0 | 5 | 5 | 5 | 0 |
| 147 | 25.0 | 5 | 5 | 3 | 0 |
| 148 | 25.0 | 5 | 4 | 5 | 0 |
| 150 | 25.0 | 5 | 5 | 5 | 0 |
| 151 | 25.0 | 5 | 5 | 5 | 0 |
| 152 | 25.0 | 5 | 5 | 5 | 0 |
| 153 | 6.3 | 5 | 4 | 5 | 0 |
| 154 | 25.0 | 5 | 5 | 5 | 0 |
| 155 | 25.0 | 5 | 5 | 4 | 0 |
| 156 | 25.0 | 5 | 5 | 5 | 0 |
| 160 | 25.0 | 5 | 5 | 5 | 0 |
| 165 | 25.0 | 5 | 5 | 5 | 0 |
| 167 | 25.0 | 5 | 5 | 3 | 0 |
| 170 | 25.0 | 5 | 5 | 5 | 1 |
| 172 | 25.0 | 5 | 5 | 5 | 0 |
| 178 | 25.0 | 5 | 5 | 5 | 0 |
| 179 | 25.0 | 5 | 5 | 5 | 0 |

TABLE 10

| Compound No. | Dose of active ingredient (g/10a) | Herbicidal effect Ec | Di | Se | So | Am | Phytotoxicity Gl | Go |
|---|---|---|---|---|---|---|---|---|
| 6 | 25.0 | 5 | 5 | 4 | 5 | 5 | 1 | 0 |
| 7 | 25.0 | 5 | 5 | 5 | 5 | 5 | 0 | 1 |
| 10 | 25.0 | 5 | 5 | 5 | 5 | 5 | 0 | 0 |
| 24 | 25.0 | 5 | 5 | 5 | 5 | 1 | 0 | 0 |
| 37 | 25.0 | 5 | 5 | 5 | 5 | 5 | 1 | 0 |
| 40 | 6.3 | 5 | 5 | 5 | 5 | 4 | 1 | 0 |
| 44 | 6.3 | 5 | 5 | 5 | 5 | 5 | 1 | 0 |
| 49 | 25.0 | 5 | 5 | 5 | 5 | 5 | 1 | 0 |
|  | 6.3 | 5 | 5 | 5 | 5 | 5 | 0 | 0 |
| 55 | 25.0 | 5 | 5 | 5 | 5 | 5 | 0 | 0 |
|  | 6.3 | 5 | 5 | 5 | 5 | 5 | 0 | 0 |
| 62 | 25.0 | 5 | 5 | 5 | 4 | 5 | 0 | 0 |
|  | 6.3 | 5 | 5 | 5 | 3 | 5 | 0 | 0 |
| 66 | 25.0 | 5 | 5 | 5 | 5 | 5 | 0 | 1 |
|  | 6.3 | 5 | 5 | 5 | 5 | 5 | 0 | 0 |
| 74 | 6.3 | 5 | 5 | 5 | 5 | 5 | 0 | 0 |
| 92 | 25.0 | 5 | 5 | 5 | 5 | 5 | 0 | 0 |
|  | 6.3 | 5 | 5 | 5 | 5 | 5 | 0 | 0 |
| 104 | 25.0 | 5 | 5 | 5 | 4 | 5 | 0 | 0 |
|  | 6.3 | 5 | 5 | 5 | 3 | 4 | 0 | 0 |
| 109 | 25.0 | 5 | 5 | 5 | 5 | 5 | 0 | 0 |
|  | 6.3 | 5 | 5 | 5 | 5 | 5 | 0 | 0 |
| 110 | 25.0 | 5 | 5 | 5 | 5 | 5 | 0 | 0 |
|  | 6.3 | 5 | 5 | 5 | 5 | 3 | 0 | 0 |
| 111 | 25.0 | 5 | 5 | 5 | 5 | 4 | 0 | 0 |
|  | 6.3 | 5 | 5 | 5 | 5 | 3 | 0 | 0 |
| 127 | 25.0 | 5 | 5 | 5 | 5 | 5 | 0 | 0 |
|  | 6.3 | 5 | 5 | 5 | 3 | 3 | 0 | 0 |
| Comparative | 25.0 | 5 | 5 | 5 | 5 | 4 | 2 | 2 |

TABLE 10-continued

| Compound No. | Dose of active ingredient (g/10a) | Herbicidal effect Ec | Di | Se | So | Am | Phytotoxicity Gl | Go |
|---|---|---|---|---|---|---|---|---|
| Compound |  |  |  |  |  |  |  |  |

We claim:

1. A 2-oxo-3-pyrroline derivative of the formula:

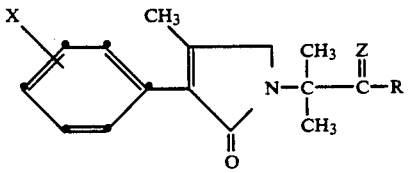

(I)

wherein

X is a hydrogen atom or a halogen atom;

Z is an oxygen atom or a group of the formula =N—OR$^1$ wherein R$^1$ is a hydrogen atom, a lower alkyl group, a benzyl group, or a phenyl group which is substituted by halogen atoms;

R is a hydrogen atom, a lower alkyl group, a benzyl group, a chloro-substituted benzyl group, a benzylidene methyl group, a group of the formula

wherein Y is a hydrogen atom, a halogen atom, a lower alkyl group, a lower haloalkyl group, or a lower alkoxy group and n is an integer of from 1 to 3, or a group of the formula ER$^2$ wherein E is an oxygen atom, a sulfur atom or a group of the formula >N—R$^3$ wherein R$^3$ is a hydrogen atom, a lower alkyl group or a lower alkenyl group; and R$^2$ is a hydrogen atom, a lower alkyl group, a lower cycloalkyl group, a lower alkenyl group, a lower alkynyl group, a benzyl group, a phenylsulfonyl group or a group of the formula

wherein G is a hydrogen atom, a halogen atom, a lower alkyl group, a lower haloalkyl group, a lower alkoxy group, a lower haloalkoxy group, a methylenedioxy group, a lower alkylthio group, a lower alkylsulfonyl group, a phenoxy group, a lower alkoxycarbonyl group, acetyl, a nitro group, a hydroxyl group, a cyano group or a dimethylamino group, and m is an integer of from 1 to 5.

2. The 2-oxo-3-pyrroline derivative according to claim 1, wherein X is a hydrogen atom, Z is an oxygen atom or a group of the formula =NOR$^1$ wherein R$^1$ is a hydrogen atom, a lower alkyl group, a benzyl group, or a phenyl group which is substituted by chlorine atoms, and R is a hydrogen atom, a lower alkyl group, a benzyl group, a chloro-substituted benzyl group, a benzylidene methyl group or a group of the formula

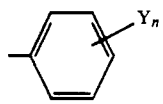

wherein Y is a hydrogen atom, a halogen atom, a lower alkyl group, a lower haloalkyl group, or a lower alkoxy group, and n is an integer of from 1 to 3.

3. The 2-oxo-3-pyrroline derivative according to claim 1, wherein X is a hydrogen atom or a halogen atom, Z is an oxygen atom or a group of the formula =N—OR¹ wherein R¹ is a hydrogen atom, a lower alkyl group, a benzyl group, or a phenyl group which is substituted by halogen atoms; R is a group of the formula ER² wherein E is an oxygen atom, a sulfur atom or a group of the formula >N—R³ wherein R³ is a hydrogen atom, a lower alkyl group, or a lower alkenyl group; and R² is a hydrogen atom, a lower alkyl group, a lower cycloalkyl group, a lower alkenyl group, a lower alkynyl group, a benzyl group, a phenylsulfonyl group, or a group of the formula

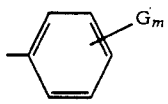

wherein G is a hydrogen atom, a halogen atom, a lower alkyl group, a lower haloalkyl group, a lower alkoxy group, a lower haloalkoxy group, a methylenedioxy group, a lower alkylthio group, a lower alkylsulfonyl group, a phenoxy group, a lower alkoxycarbonyl group, acetyl, a nitro group, a hydroxyl group, a cyano group or a dimethylamino group, and m is an integer of from 1 to 5.

4. The 2-oxo-3-pyrroline derivative according to claim 1, wherein R is a 3,5-dichlorophenyl group.

5. A 2-oxo-3-pyrroline derivative having the formula:

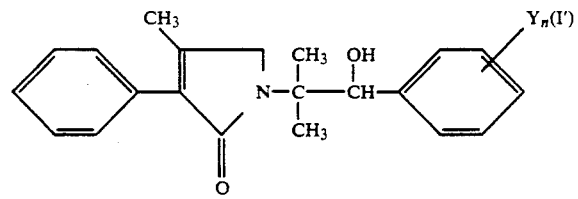

wherein Y is a hydrogen atom, a halogen atom, a lower alkyl group, a lower haloalkyl group or a lower alkoxy group, and n is an integer of from 1 to 5.

6. A 2-oxo-3-pyrroline derivative having the formula:

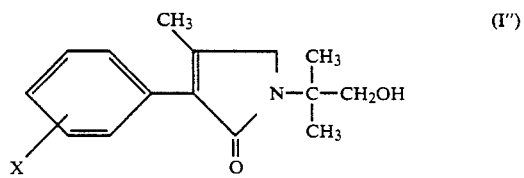

wherein X is a hydrogen atom or a halogen atom.

7. A herbicidal composition comprising an inert carrier and a herbicidally effective amount of a 2-oxo-3-pyrroline derivative as defined in claim 1.

* * * * *